(12) United States Patent
Bonutti et al.

(10) Patent No.: US 8,641,660 B2
(45) Date of Patent: Feb. 4, 2014

(54) METHODS AND DEVICES FOR CONTROLLING BIOLOGIC MICROENVIRONMENTS

(75) Inventors: Peter M. Bonutti, Effingham, IL (US); Justin E. Beyers, Effingham, IL (US)

(73) Assignee: P Tech, LLC, Effingham, IL (US)

( * ) Notice: Subject to any disclaimer, the term of this patent is extended or adjusted under 35 U.S.C. 154(b) by 1166 days.

(21) Appl. No.: 11/867,679

(22) Filed: Oct. 4, 2007

(65) Prior Publication Data
US 2008/0086072 A1 Apr. 10, 2008

Related U.S. Application Data

(60) Provisional application No. 60/828,084, filed on Oct. 4, 2006.

(51) Int. Cl.
*A61M 31/00* (2006.01)

(52) U.S. Cl.
USPC .............................. 604/66; 604/65; 604/67

(58) Field of Classification Search
USPC .......................... 604/65–67, 20, 21
See application file for complete search history.

(56) References Cited

U.S. PATENT DOCUMENTS

| | | | |
|---|---|---|---|
| 3,837,922 A | 9/1974 | Ng et al. | |
| 4,326,529 A | 4/1982 | Doss et al. | |
| 4,326,535 A | 4/1982 | Steffel et al. | |
| 4,719,919 A | 1/1988 | Marchosky et al. | |
| 5,062,841 A | 11/1991 | Siegel | |
| 5,087,243 A | 2/1992 | Avitall | |
| 5,109,850 A | 5/1992 | Blanco et al. | |
| 5,269,785 A | 12/1993 | Bonutti | |
| 5,320,611 A | 6/1994 | Bonutti et al. | |
| 5,329,846 A | 7/1994 | Bonutti | |
| 5,329,924 A | 7/1994 | Bonutti | |
| 5,335,650 A | 8/1994 | Shafer et al. | |
| 5,349,956 A | 9/1994 | Bonutti | |
| 5,542,423 A | 8/1996 | Bonutti | |
| 5,593,425 A | 1/1997 | Bonutti et al. | |
| 5,674,240 A | 10/1997 | Bonutti et al. | |
| 5,730,720 A | 3/1998 | Sites et al. | |
| 5,810,770 A * | 9/1998 | Chin et al. | 604/65 |
| 5,948,002 A | 9/1999 | Bonutti | |
| 5,961,499 A | 10/1999 | Bonutti et al. | |
| 6,176,842 B1 * | 1/2001 | Tachibana et al. | 604/22 |
| 6,178,349 B1 | 1/2001 | Kieval | |
| 6,325,774 B1 | 12/2001 | Bene et al. | |
| 6,332,221 B1 | 12/2001 | Gracey | |
| 6,338,730 B1 | 1/2002 | Bonutti et al. | |
| 6,371,970 B1 | 4/2002 | Khosravi et al. | |
| 6,402,689 B1 | 6/2002 | Scarantino et al. | |
| 6,564,101 B1 | 5/2003 | Zikria | |
| 6,589,159 B2 | 7/2003 | Paturu | |

(Continued)

OTHER PUBLICATIONS

Margaret Pak et al., Micro Fuel Cells, 19 pgs, Business Intelligence Program © May 2002.

*Primary Examiner* — Bhisma Mehta
*Assistant Examiner* — Imani Hayman
(74) *Attorney, Agent, or Firm* — Fleit Gibbons Gutman Bongini & Bianco PL; Lucas Wenthe; Paul Bianco

(57) ABSTRACT

A microenvironment of a biological body is controlled, and more particularly, is measured, changed, and monitored with respect to temperature, pH level, moisture and other tissue parameters of a region of the body while, optionally, administering a therapeutic agent to that region.

18 Claims, 26 Drawing Sheets

(56) References Cited

U.S. PATENT DOCUMENTS

| | | |
|---|---|---|
| 6,589,198 B1 | 7/2003 | Soltanpour |
| 6,600,941 B1 | 7/2003 | Khuri |
| 6,702,821 B2 | 3/2004 | Bonutti |
| 6,770,078 B2 | 8/2004 | Bonutti |
| 6,820,614 B2 | 11/2004 | Bonutti |
| 6,873,268 B2 | 3/2005 | Lebel et al. |
| 6,890,312 B1 | 5/2005 | Priester et al. |
| 6,961,620 B2 | 11/2005 | Rioux et al. |
| 7,004,933 B2 | 2/2006 | McDaniel |
| 7,004,961 B2 | 2/2006 | Wong et al. |
| 7,056,318 B2 | 6/2006 | Black |
| 7,104,996 B2 | 9/2006 | Bonutti |
| 7,160,637 B2 | 1/2007 | Chiao et al. |
| 7,226,442 B2 | 6/2007 | Sheppard et al. |
| 7,241,457 B2 | 7/2007 | Chen et al. |
| 2003/0181800 A1 | 9/2003 | Bonutti |
| 2005/0209564 A1* | 9/2005 | Bonner et al. ............. 604/173 |
| 2005/0267565 A1 | 12/2005 | Dave et al. |
| 2006/0089646 A1 | 4/2006 | Bonutti |
| 2007/0270833 A1 | 11/2007 | Bonutti et al. |

* cited by examiner

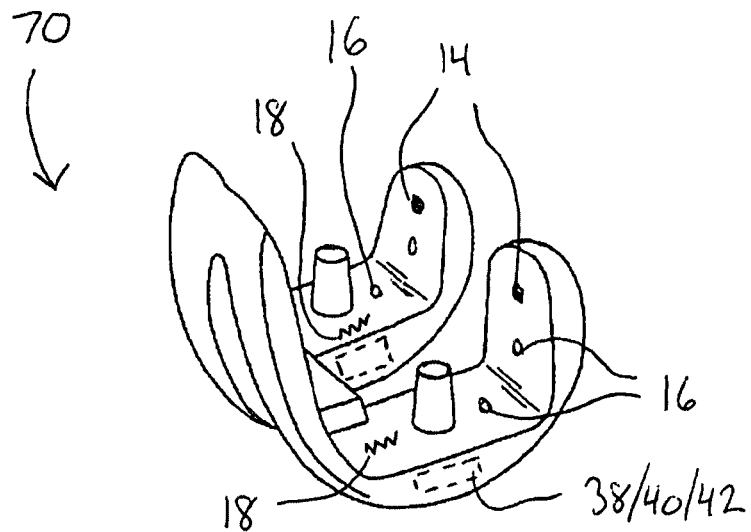
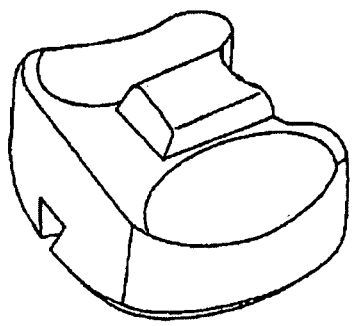
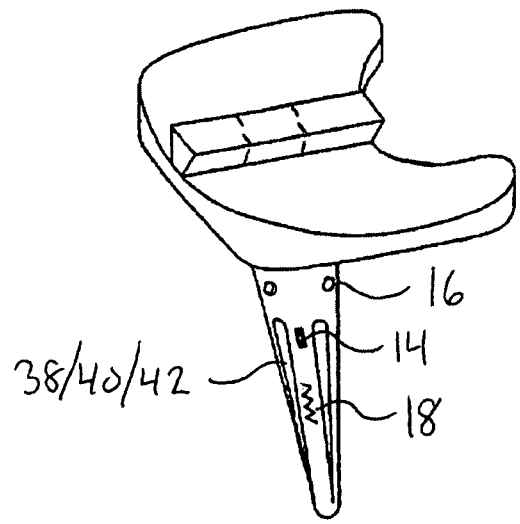
FIG. 7

METHODS AND DEVICES FOR CONTROLLING BIOLOGIC MICROENVIRONMENTS

CROSS-REFERENCE TO RELATED APPLICATIONS

This application claims the benefit of U.S. Provisional Patent Application 60/828,084 to the same inventor, filed Oct. 4, 2006, entitled METHODS AND DEVICES FOR CONTROLLING BIOLOGIC MICROENVIRONMENTS, the entire contents of which are incorporated herein by reference.

FIELD OF THE INVENTION

The invention relates to controlling a microenvironment of a biological body, and more particularly, to measuring, changing, and monitoring the temperature, pH level, moisture and other tissue parameters of a region of the body while, optionally, administering a therapeutic agent to that region.

BACKGROUND OF THE INVENTION

The human body and bodies of other mammals naturally maintain a certain level of temperature, pH, humidity, etc. The normal temperature of the human body is, for example, 98.6 degrees Fahrenheit. This temperature level, however, is not consistent throughout the entire body. Different body regions may be higher or lower than 98.6 degrees. Acidity levels also vary. Certain body parts, such as the stomach or intestines may have a different pH level than the brain or heart. Also, temperature and acidity levels vary in the body throughout the day, depending on the level of activity of a particular person. A person sleeping will have different pH levels than the same person exercising.

Other factors that determine the microenvironment of the body is disease, damage, and injury to tissue. The body may somewhat fluctuate the microclimate of tissue during healing, to fight infection, and to resist or kill a foreign object. However, augmenting the body's ability to control the microenvironment enhances tissue healing. Some patent documents disclose various methods, devices, and reasons for controlling the body's temperature, pH level, moisture, and other microclimate parameters.

U.S. Pat. No. 7,056,318 entitled "Temperature Controlled Heating Device and Method to Heat a Selected Area of a Biological Body" discloses a heating device and method for controlling a temperature in a selected area of a body part to obtain a temperature effect within the selected area for therapeutic or medical purposes. It includes temperature generating means to generate a temperature in the selected area. It also includes temperature detecting means to detect the generated temperature from the selected area. It further includes temperature controlling means to control the temperature generating means to maintain the generated temperature within a range of a desired temperature. The device and method prevent irreversibly damaging or overheating the selected area or the tissue surrounding the selected area. It is advantageous to applications where there is a need to accurately control the temperature in a selected area in a biological body, for instance, to activate or evaporate a temperature sensitive agent in the selected area.

U.S. Pat. No. 7,004,961 entitled "Medical Device and Method for Temperature Control and Treatment of the Brain and Spinal Cord" discloses a medical device having a thermostat for temperature measurement, irrigation/aspiration ports for fluid exchange and application of therapeutic modalities, a pressure manometer for pressure measurement, and an external system for control of temperature, pressure, and flow rate. When applied to the central nervous system (CNS), this device can be used in hypothermia or hyperthermia applications, the exchange of cerebral spinal fluid (CSF), the application of treatment modalities, and the insertion of a ventriculostomy or ventriculostomy-like unit. When applied to spinal cord applications, this device can provide temperature control and a method for application of treatment modalities by using a venting device placed in the space surrounding the spinal cord, a device with similar instrumentation to measure temperature and pressure.

U.S. Pat. No. 7,004,933 entitled "Ultrasound Enhancement of Percutaneous Drug Absorption" discloses a system for enhancing and improving the transcutaneous or transdermal delivery of topical chemicals or drugs. A disposable container contains a substantially sterile unit dose of an active agent adapted for a single use in a medical treatment. The unit dose is formulated to enhance transport of the active agent through mammalian skin when the active agent is applied to the skin and the skin is exposed to light and/or ultrasound defined by at least one specific parameter.

U.S. Pat. No. 6,961,620 entitled "Apparatus and Methods for Assisting Ablation of Tissue Using Magnetic Beads" discloses a system for treating tissue includes a source of conductive and/or magnetic beads, a first member, e.g., a catheter or cannula, coupled to the source of magnetic beads, and a second member, e.g., a catheter or cannula, carrying a magnet on its distal end. The system is used for ablating or otherwise treating tissue within a target tissue region including a blood vessel contacting or passing therethrough. Magnetic beads are introduced into the target tissue region, e.g., using the first member, and a magnetic field is generated within the target tissue region, e.g., using the second member, to cause the magnetic beads to migrate towards a wall of the vessel. Energy is delivered into the target tissue region, e.g., to heat tissue therein, and the magnetic beads may attenuate or enhance treatment of tissue adjacent to the vessel.

U.S. Pat. No. 6,600,941 entitled "Systems and Methods of pH Tissue Monitoring" discloses the use of pH measurements of tissue as a system for controlling diagnostic and/or surgical procedures. The invention also relates to an apparatus used to perform tissue pH measurements. Real time tissue pH measurements can be used as a method to determine ischemic segments of the tissue and provide the user with courses of conduct during and after a surgical procedure. When ischemia is found to be present in a tissue, a user can affect an optimal delivery of preservation fluids to the site of interest and/or effect a change in the conduct of the procedure to raise the pH of the site.

U.S. Patent Publication No. 2005/0267565 entitled "Biodegradable Medical Implant with Encapsulated Buffering Agent" discloses a medical device for placement at a site in a patient's body and for controlling pH levels at the site in the patient's body includes one or more structural components made of a first biodegradable and/or bioabsorbable material or, alternatively, one or more structural components having a coating thereon made of a first biodegradable and/or bioabsorbable material. The device also includes a buffering agent and at least one second biodegradable and/or bioabsorbable material on or in the one or more structural components, or alternatively, on or in the coating on the one or more structural components. The at least one second biodegradable and/or bioabsorbable material encapsulates the buffering agent and the buffering agent is dispersed from the at least one second biodegradable and/or bioabsorbable material in response to hydrolysis of the first biodegradable and/or bioabsorbable material. Additionally, the device can include a drug that is either also encapsulated by the at least one second biodegradable and/or bioabsorbable material or is included with the first biodegradable and/or bioabsorbable material There exists a need for apparatus and methods for controlling the biologic microenvironment of a body region by measuring, changing, and monitoring the temperature, pH level, moisture level, and other microenvironment parameters and simultaneously delivering a pharmaceutical/therapeutic agent.

SUMMARY OF THE INVENTION

The present invention relates to devices and methods for controlling microenvironments in living organisms. The microenvironment (or microclimate) of a region of the body is defined as those characteristics which create the conditions necessary for cells to function. Such characteristics may include temperature, pH level, moisture, humidity, oxygen tension, oxygenase, carbon dioxide tension, rate of blood flow, nutrient-content, osmolarity, pressure, vascular permeability, electrical charge, and the presence of pharmaceutical agents. Some of these characteristics, like temperature, may be naturally controlled by the body. However, as a result of disease, age, injury, or surgery, the body may require augmentation for controlling the microenvironment of a body region. The present invention provides for measuring, changing, and monitoring microenvironment parameters. Through the use of sensors, implanted or externally positioned, the parameters may be measured. A physician or sensors/microprocessor determines whether the measured levels are appropriate for the selected body region. If not, the levels may be adjusted. Continuous monitoring of the microenvironment creates a feedback loop so that the microenvironment characteristics may be selectively controlled, manually or automatically.

Optimizing the microenvironment with the devices and methods of the present invention may be used to enhance or improve the effect of therapeutic/pharmaceutical agents, improve the outcome of a surgical procedure or intervention, enhance the results of a surgical implant, optimize cell or tissue ingrowth when using cell therapy or gene therapy, and other advantages which are described in relation to the exemplary embodiments. Controlling the microenvironment with this multimodal approach may be performed preoperatively, during surgical treatment, and postoperatively.

Other benefits for controlling the microenvironment include effecting cell receptors, effecting hormone release, effecting tissue healing, effecting the ability of bacteria to multiple or reduce, effecting virus activity, stimulating white blood cells enzyme release, stimulating white blood cell phagocytosis or migration, and managing pain.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 7 is a perspective view knee replacement components designed for controlling the microenvironment of a knee joint;

DETAILED DESCRIPTION OF THE INVENTION

The present invention relates to devices and methods for controlling microenvironments in living organisms. Characteristics of the microenvironment that may be controlled include temperature, pH, moisture, humidity, oxygen-content, oxygenase, carbon dioxide-content, rate of blood flow, nutrient-content, osmolarity, pressure, vascular permeability, electrical charge, and the presence of pharmaceutical or therapeutic agents. These characteristics may be measured, changed, and monitored automatically and/or selectively by a physician to obtain the optimal environment for a particular body region. Continuous monitoring of the microenvironment creates a feedback loop so that the microenvironment characteristics may be continuously controlled.

Implanted Systems

Figure 1:
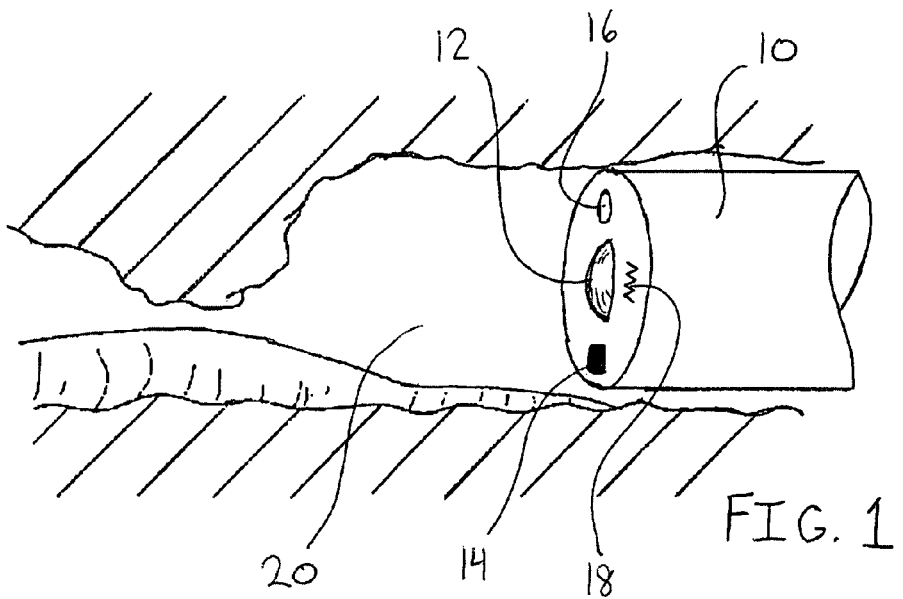
FIG. 1 illustrates an endoscope positioned in a body region for controlling the microclimate thereof.

Referring to FIG. 1, a surgical instrument is shown positioned in a region of a living body. The region naturally includes tissue which requires certain levels of environmental parameters for proper function. These parameters may include temperature, pH level, moisture, humidity, oxygen tension, carbon dioxide tension, rate of blood flow, nutrient-content, the presence of pharmaceutical agents, etc. Through the use of various surgical instruments, these parameters may be measured, changed, and monitored.

An endoscope 10, shown in FIG. 1, includes a viewing port 12 such as a camera lens, a sensor 14, a delivery port 16, and a heating/cooling unit 18. Cooling units may include a Peltier cooler, optionally including means to dissipate or redirect heat generated, including a heat sink, and or a liquid circulation system. The viewing port 12 allows the physician to precisely insert the endoscope 10 in the region 20 and provides visualization of the microenvironment region. The sensor 14 is designed to respond to physical stimuli and transmit resulting impulses for interpretation, recording, or operating control. A display screen (not shown) may be positioned outside the living body and in view of the physician. The screen and related electronic components process and display the sensor readings. The sensor 14 may be a temperature sensor, pH level sensor, moisture sensor, oxygen sensor, carbon dioxide sensor, or any other sensor to measure microenvironment characteristics. The delivery port 16 is in fluid communication with a lumen within the endoscope and a reservoir (not shown). The delivery port and reservoir 16 are configured for delivering a liquid, gas, gel, powder, and/or solid to affect the microenvironment of the region 20.

Therapeutic substances to control the microenvironment may include antibiotics, hydroxypatite, anti-inflammatory agents, steroids, antibiotics, analgesic agents, chemotherapeutic agents, bone morphogenetic protein, demineralized bone matrix, collagen, growth factors, autogenetic bone marrow, progenitor cells, calcium sulfate, immu-suppressants, fibrin, osteoinductive materials, apatite compositions, fetal cells, stem cells, enzymes, proteins, hormones, germicides, non-proliferative agents, anti-coagulants, anti-platelet agents, Tyrosine Kinase inhibitors, anti-infective agents, anti-tumor agents, anti-leukemic agents, and combinations thereof.

The heating/cooling unit 18 of the endoscope permits the physician to adjust the temperature of the microenvironment. The unit 18 may be a resistive heater, an ultrasonic heater, IR heater, RF heater, microwave heater, or a convection/conduction cooling device. By controlling the temperature of the region, other parameters, such as pH, blood flow rate, etc., may be controlled as a result. For example, raising the temperature of the microenvironment region, the pH level may be increased.

Figure 2:
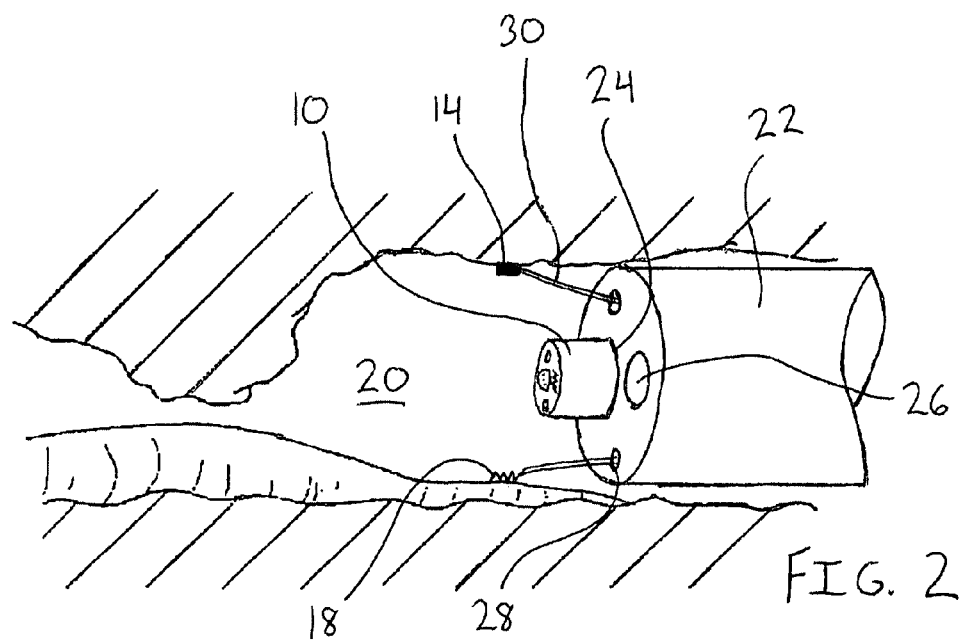
FIG. 2 shows a multi-lumen catheter inserted in a body region and having an endoscope and sensors extending therefrom.

In FIG. 2, another embodiment for controlling the microenvironment is shown. A multi-lumen catheter or cannula 22 includes an endoscope channel 24, a surgical instrument channel 26, and a plurality of microenvironment-control channels 28. The endoscope channel 24 is configured to receive an endoscope 10 like that of FIG. 1. The instrument channel 26 provides access for a physician to insert medical instruments into the region 20 of the body. The microenvironment-control channels 28 are configured for insertion of sensors 14 and heating/cooling units 18 into the microenvironment region 20. The sensors 14 and heating/cooling units 18 are of the types previously described. The microenvironment-control channels 28 may also be configured for delivery of gases, liquids, gels, and solids. Therapeutic agents may be delivered via the microenvironment-control channels.

To control the microenvironment of the region, a physician may utilize the devices of FIGS. 1 and 2 as follows. A small incision may be made in the skin of the patient, and soft tissue may be distracted with a trocar or guidewire to create a path to the region 20 requiring microenvironment adjustment. The cannula may be inserted through the incision and in the path. For a region accessible through an orifice of the body, the cannula may be positioned through the orifice without needing to make an incision in the skin. With the cannula positioned in the body, the endoscope 10 may be inserted in the endoscope channel of the cannula. The endoscope 10 may be steered by the physician to locate and analyze the desired body region. A sensor 14 and/or heating/cooling unit 18 may be inserted into the microenvironment-control channels 28 of the cannula.

As shown in FIG. 2, a sensor 14 is deployed from the cannula 22 and positioned against tissue in the body region 20. Also, a heating/cooling unit 18 is deployed from the cannula 22 and positioned against the tissue. A connection member 30 such as a wire or plastic rod carries the sensor 14 and/or heating/cooling unit 18. Electrical or optical wiring may be located within or adjacent the connection member 30 to carry signals between a control unit (not shown) and the sensor 14 and heating/cooling unit 18. Based on the measured microenvironment parameters of the region, the physician may selectively change one or more of the parameters and/or administer one or more therapeutic agents to the region.

The surgical instruments of FIGS. 1 and 2 may be utilized with minimally invasive surgery techniques disclosed in U.S. Pat. Nos. 6,702,821; 6,770,078; and 7,104,996. These patent documents disclose, inter alia, apparatus and methods for minimally invasive medical procedures. U.S. Pat. Nos. 6,702, 821; 6,770,078; and 7,104,996 are hereby incorporated by reference.

Figure 3:
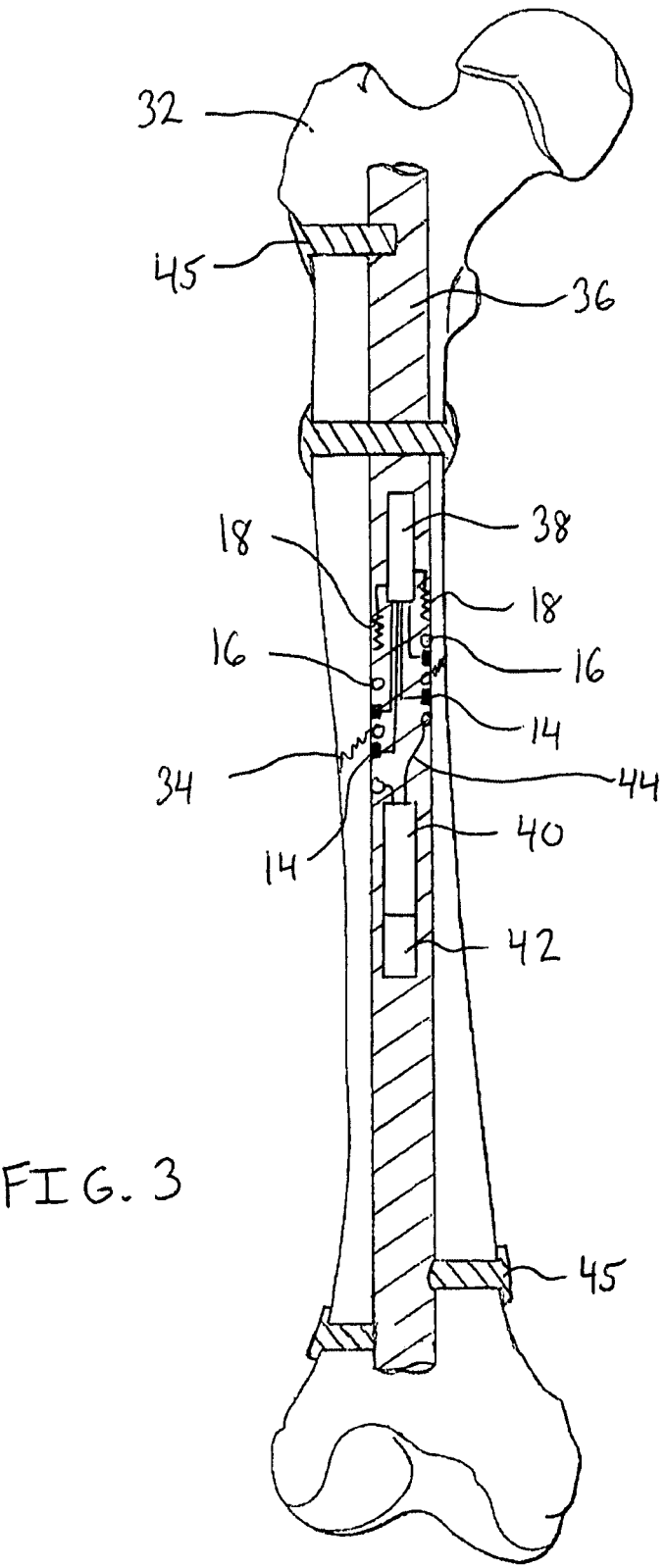
FIG. 3 illustrates an intramedullary rod designed for controlling the microenvironment of a bone fracture.

Referring now to FIG. 3, another apparatus for controlling the microenvironment of a body region is shown. In FIGS. 1 and 2, the microenvironment of soft tissue was manipulated, while in FIG. 3 the microenvironment of hard tissue, such as bone 32, is controlled. The bone 32 has a fracture 34 or other injury therein. The implant of FIG. 3 is an intramedullary rod 36 which stabilizes the fractured bone. The IM rod 36 may be made of metallic, ceramic, or polymeric material. The IM rod 36 may include thermoplastic material which is formable with the application of heat. Patent documents which further describe such thermoplastic implants include U.S. patent application Ser. No. 11/416,618 filed May 3, 2006 and U.S. Provisional Patent Application Nos. 60/765,857 filed Feb. 7, 2006; 60/784,186 filed Mar. 21, 2006; and 60/810,080 filed Jun. 1, 2006, all of which are hereby incorporated by reference.

The IM rod 36 of the present invention includes sensors 14, heating/cooling units 18, and an electronic controller 38. The sensors 14 may be temperature sensors, pH sensors, moisture sensors, oxygen sensors, carbon dioxide sensors, or other sensors to measure microenvironment characteristics. The heating/cooling units 18 may be resistive heaters, ultrasonic heaters, IR heaters, RF heaters, microwave heaters, or convection/conduction cooling devices. Both the sensors 14 and heating/cooling units 18 may be controlled by the electronic controller 38, either automatically based on predetermined measurements or manually via remote control. Manual control of the implanted electronic processor may be achieved through IR, RF, or microwave energy or through an implanted wire.

The IM rod 36 also includes delivery ports 16, a reservoir 40, and a reservoir controller 42. Each delivery port 16 is in fluid communication with the reservoir 40 by way of piping 44. The delivery ports 16 and reservoir 40 are configured for delivering a liquid, gas, gel, and/or solid to affect the microenvironment of the region. The substance administered through the delivery ports may be any of the agents or substances disclosed herein. The reservoir controller 42 manipulates the release rate and release period of the substance(s) in the reservoir 40. The reservoir controller 42 and electronic processor 38 may be linked together to function as a single system. That is, the reservoir controller and electronic processor work together to control the microenvironment of the body region. Alternatively, the reservoir controller and electronic processor may be physically integrated into one assembly.

The microenvironment of a fracture 34 of a bone 32 may be controlled with the IM rod 36 of FIG. 3 by the following method. The medullary canal of the fractured bone 32 is cleared out and formed to receive the IM rod 36. The rod 36 is inserted into the medullary canal such that the sensors 14, heating/cooling units 18, and delivery ports 16 are adjacent the fracture 34. If the bone includes multiple fractures, then the sensors, units, and delivery ports may be located at various locations along the length of the rod. The IM rod 36 is secured to the bone with fasteners 45. The fasteners 45 may lock mechanically in the bone and/or may thermally bond to the bone and rod. Examples of mechanical and thermal fasteners are disclosed in the thermoplastic implant documents already incorporated by reference.

With the rod 36 implanted, the microclimate may be controlled to create an optimal healing environment. For example, a sensor 14 may measure a microenvironment parameter and based on predetermined levels, the electronic processor 38 may instruct the reservoir controller 42 to release a substance from the reservoir 40. Substances which may be beneficial to a fractured bone may include bone morphogenetic proteins, antibiotics, hydroxyapitate, and other bone healing agents. Agents that increase or decrease the pH level may also be delivered. The electronic processor 38 may also instruct a heating/cooling unit 18 to change the temperature of the body region. Controlling the microenvironment may be performed automatically by microprocessors based on preset parameter levels and input signals from the sensors. The microenvironment may alternatively, or additionally, be controlled by a physician via remote control. The physician may use RF, microwave, or IR energy to transmit instructions to the microprocessors in the IM rod.

Figure 4:
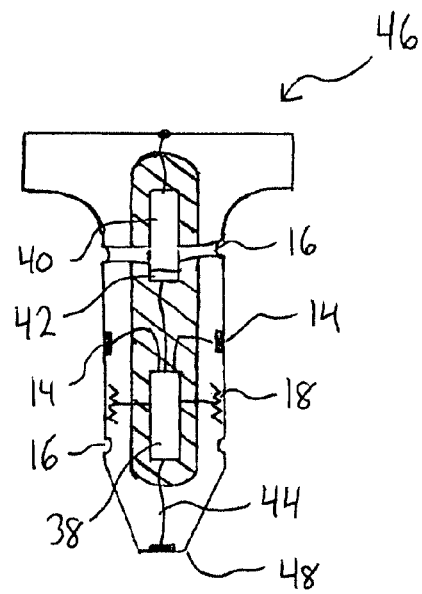
FIG. 4 is a cross sectional view of a fastener configured for controlling the microenvironment.

For use with the IM rod 36 of FIG. 3 or any other implant, a microenvironment-controllable fastener 46 is provided in FIG. 4. The fastener 46 may be made of metallic, ceramic, polymeric, composite, or thermoplastic material. The fastener 46 includes sensors 14, heating/cooling units 18, and electronic controllers 38 similar to those of FIG. 3. The sensors 14 may be temperature sensors, pH sensors, moisture sensors, oxygen sensors, carbon dioxide sensors, or other sensors to measure microenvironment characteristics. The heating/cooling units 18 may be resistive heaters, ultrasonic heaters, IR heaters, RF heaters, microwave heaters, or convection/conduction cooling devices. Both the sensors 14 and heating/cooling units 18 are controlled by the electronic controller 38, either automatically based on predetermined measurements or manually via remote control. Manual control on the implanted electronic processor may be achieved through IR, RF, or microwave energy or through an implanted wire.

The fastener 46 also includes delivery ports 16, a reservoir 40, and a reservoir controller 42. Each delivery port 16 is in fluid communication with the reservoir 40 via piping 44. The delivery ports 16 and reservoir 40 are configured for delivering a liquid, gas, gel, and/or solid to affect the microenvironment of the region. The substance administered through the delivery ports may be any of the substances disclosed herein. The reservoir controller 42 manipulates the release rate and release period of the substance(s) in the reservoir. The reservoir controller 42 and electronic processor 38 may be linked together to function as a single system. That is, the reservoir controller and electronic processor work together to control the microenvironment of the body region. Alternatively, the reservoir controller and electronic processor may be physically integrated into one assembly.

In use, the microenvironment of soft or hard tissue may be controlled with the fastener 46 of FIG. 4. A bore may be created in the tissue, and the fastener 46 positioned in the bore. Alternatively, the fastener 46 may include a tissue-piercing tip 48 which eliminates the need to create a bore before implanting the fastener in the tissue. If the tissue includes multiple areas for climate control, then the sensors 14, units 18, and delivery ports 16 may be located at various locations along the length of the fastener. With the fastener implanted, the microclimate may be controlled to create an optimal healing environment.

In an exemplary embodiment, a sensor 14 may measure a microenvironment parameter and based on predetermined levels, the electronic processor 38 may instruct the reservoir controller 42 to release one or more substances from the reservoir 40. The electronic processor 38 may also instruct a heating/cooling unit 18 to change the temperature of the tissue. Controlling the microenvironment around the fastener 46 may be performed automatically by microprocessors based on preset parameter levels and input signals from the sensors. The microenvironment may alternatively, or additionally, be controlled by a physician via remote control. The physician may use RF, microwave, or IR energy to transmit instructions to the microprocessors in the fastener.

Figure 5:
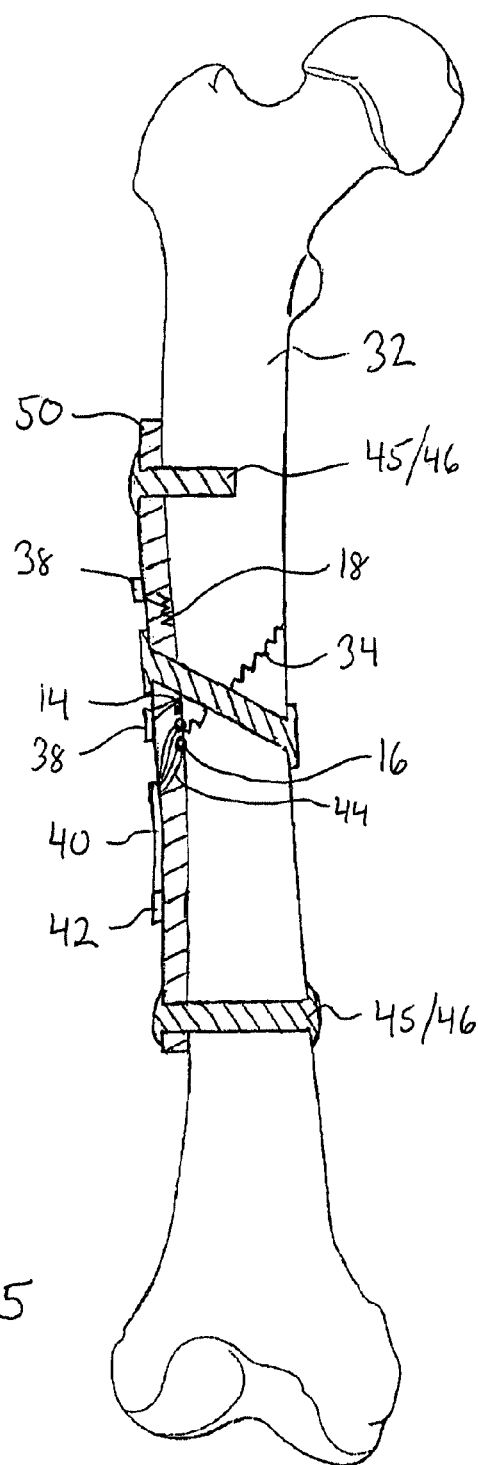
FIG. 5 shows a bone plate designed for controlling the microenvironment of a bone fracture.

The fractured bone of FIG. 3 may alternatively, or additionally, be stabilized by a microenvironment-controlling rigid plate 50 of FIG. 5. The fastener 46 of FIG. 4 and IM rod 36 of FIG. 3 utilized internal microprocessors, sensors, and units. The implant 50 of FIG. 5 may include externally mounted microenvironment-controlling devices. The rigid fixation plate may be made of metallic, ceramic, composite, polymeric, or thermoplastic material. The plate 50 includes sensors 14, heating/cooling units 18, and an electronic controller 38. The sensors 14 may be temperature sensors, pH sensors, moisture sensors, oxygen sensors, carbon dioxide sensors, or other sensors to measure microenvironment characteristics. The heating/cooling units 18 may be resistive heaters, an ultrasonic heaters, IR heaters, RF heaters, microwave heaters, or convection/conduction cooling devices. Both the sensors 14 and heating/cooling units 18 are controlled by the electronic controller 38, either automatically based on predetermined measurements or manually with a wire or wireless (IR, RF, or microwave energy).

The rigid plate 50 also includes delivery ports 16, a reservoir 40, and a reservoir controller 42. Each delivery port 16 is in fluid communication with the reservoir 40 by way of piping 44. The delivery ports 16 and reservoir 40 are configured for delivering a liquid, gas, gel, and/or solid to affect the microenvironment of the region. The substance administered through the delivery ports 16 may be any of the substances disclosed herein. The reservoir controller 42 manipulates the release rate and release period of the substance(s) in the reservoir. The reservoir controller 42 and electronic processor 38 may be linked together to function as a single system. That is, the reservoir controller and electronic processor work together to control the microenvironment of the body region. Alternatively, the reservoir controller and electronic processor may be physically integrated into one assembly.

The microenvironment of the bone fracture 34 may be controlled with the rigid plate 50 alone, or with a combination of the IM rod 36, rigid plate 50, and/or fastener 46. In use, the rigid plate 50 may be positioned against the bone 32 such that the sensors 14, heating/cooling units 18, and delivery ports 16 are adjacent the fracture 34. If the bone 32 includes multiple fractures, then the sensors, units, and delivery ports may be located at various locations along the length of the plate. The plate 50 may be secured to the bone with fasteners 45/46. The fasteners may lock mechanically in the bone and/or may thermally bond to the bone and rod. Examples of mechanical and thermal fasteners are disclosed in the thermoplastic implant documents already incorporated by reference.

Where multiple implants are employed, it is contemplated that various components of the system, as described herein, may be distributed among the implanted elements. For example, each fastener may comprise a reservoir and controllable port, and an intramedullary implant may contain a controller, receiver, transmitter, and port controller, connected to the ports in the fasteners. A plate may further contain an energy source in communication with the other implants, or may support or contain any of the other components mentioned. Additional combinations and permutations for distributing components in accordance with the invention are contemplated, while serving the objects of the invention.

With the plate 50 implanted, the microclimate may be controlled to create an optimal healing environment. For example, a sensor 14 may measure a microenvironment parameter and based on predetermined levels, the electronic processor 38 may instruct the reservoir controller 42 to release an agent or substance from the reservoir 40. Substances which may be beneficial to a fractured bone may include bone morphogenetic proteins, antibiotics, hydroxyapitate, and other bone healing agents. The electronic processor 38 may also instruct a heating/cooling unit 18 to change the temperature of the body region. Controlling the microenvironment may be performed automatically by microprocessors based on preset parameter levels and input signals from the sensors. The microenvironment may alternatively, or additionally, be controlled by a physician via remote control. The physician may use RF, microwave, or IR energy to transmit instructions to the microprocessors on the plate.

Figure 6:
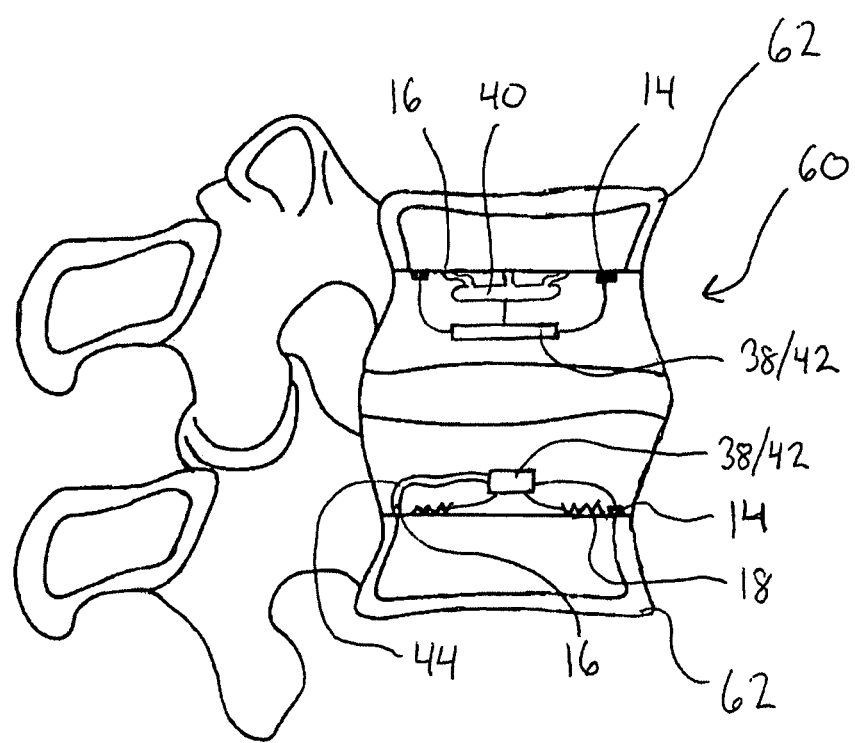
FIG. 6 illustrates a spinal implant constructed to control the microenvironment of a spinal region.

In addition to controlling the microenvironment of a bone fracture, a microenvironment-controlling implant may be utilized to heal tissue following joint replacement surgery. FIG. 6 shows an intervertebral disc replacement component 60. The disc implant 60 may be advantageously made of a biocompatible material, including metallic, ceramic, composite, polymeric, or thermoplastic material. Various intervertebral implants and other implants which may include microenvironment-controlling devices are disclosed in U.S. patent application Ser. No. 11/258,795 filed Oct. 26, 2005, which is hereby incorporated by reference. The intervertebral implant 60 of the present invention may include sensors 14, heating/cooling units 18, and an electronic controller 38. The sensors 14 may be temperature sensors, pH sensors, moisture sensors, oxygen sensors, carbon dioxide sensors, or other sensors to measure microenvironment characteristics. The heating/cooling units 18 may be resistive heaters, an ultrasonic heaters, IR heaters, RF heaters, microwave heaters, or convection/conduction or electronic cooling devices. Both the sensors 14 and heating/cooling units 18 are controlled by the electronic controller 38, either automatically based on predetermined measurements or manually via remote control. Manual control on the implanted electronic processor may be achieved through IR or RF energy or through an implanted wire.

The intervertebral implant 60 also includes delivery ports 16, a reservoir 40, and a reservoir controller 42. Each delivery port 16 is in fluid communication with the reservoir 40 via piping 44. The delivery ports 16 and reservoir 40 are configured for delivering a liquid, gas, gel, and/or solid to affect the microenvironment of the intervertebral region. The substance administered through the delivery ports 16 may be any of the substances disclosed herein. The reservoir controller 42 manipulates the release rate and release period of the substance(s) in the reservoir. The reservoir controller 42 and electronic processor 38 may be linked together to function as a single system. That is, the reservoir controller and electronic processor work together to control the microenvironment of the body region. Alternatively, the reservoir controller and electronic processor may be physically integrated into one assembly.

The microenvironment of adjacent vertebral bodies 62 may be controlled with the implant 60 of FIG. 6 as follows. After the vertebral bodies 62 have been prepared/cut, the implant 60 is positioned against the superior and inferior bones such that the sensors 14, heating/cooling units 18, and delivery ports 16 are adjacent the bone. The implant 60 may be secured to the bone with fasteners. The fasteners may lock mechanically in the bone and/or may thermally bond to the bone and rod. Examples of mechanical and thermal fasteners are disclosed in the thermoplastic implant documents already incorporated by reference.

With the disc component 60 implanted, the microclimate may be controlled to enhance tissue healing. For example, a sensor 14 may measure a microenvironment parameter and based on predetermined levels, the electronic processor 38 may instruct the reservoir controller 42 to release a substance from the reservoir 40. Substances which may be beneficial to a fractured bone may include bone morphogenetic proteins, antibiotics, hydroxyapitate, and other bone healing agents. The electronic processor 38 may also instruct a heating/cooling unit 18 to change the temperature of the body region. Controlling the microenvironment may be performed automatically by microprocessors based on preset parameter levels and input signals from the sensors. The microenvironment may alternatively, or additionally, be controlled by a physician via remote control. The physician may use RF, microwave, or IR energy to transmit instructions to the microprocessors in the disc implant.

In addition to intervertebral implants, other joint replacement components may include microenvironment-controlling devices. FIG. 7 shows a total knee replacement implant 70 with climate adjusting means of the present invention. The knee implant 70 may be made of metallic, ceramic, composite, polymeric, or thermoplastic material. Other materials and structural characteristics for knee replacement components are disclosed in U.S. Pat. No. 7,104,996 issued Sep. 12, 2006 and its continuations and divisionals, all of which are hereby incorporated by reference. The knee components 70 include sensors 14, heating/cooling units 18, and an electronic controller 38. The sensors 14 may be temperature sensors, pH sensors, moisture sensors, oxygen sensors, carbon dioxide sensors, or other sensors to measure microenvironment characteristics. The heating/cooling units 18 may be resistive heaters, an ultrasonic heaters, IR heaters, RF heaters, microwave heaters, or convection/conduction cooling devices. Both the sensors 14 and heating/cooling units 18 are controlled by the electronic controller 38, either automatically based on predetermined measurements or manually via remote control. Manual control on the implanted electronic processor may be achieved through IR, RF, or microwave energy or through an implanted wire.

The knee replacement components 70 also include delivery ports 16, a reservoir 40, and a reservoir controller 42. Each delivery port 16 is in fluid communication with the reservoir 40 by way of piping 44. The delivery ports 16 and reservoir 40 are configured for delivering a liquid, gas, gel, and/or solid to affect the microenvironment of the region. The substance administered through the delivery ports 16 may be any of the agents or substances disclosed herein. The reservoir controller 42 manipulates the release rate and release period of the substance(s) in the reservoir. The reservoir controller 42 and electronic processor 38 may be linked together to function as a single system. That is, the reservoir controller 42 and electronic processor 38 work together to control the microenvironment of the body region. Alternatively, the reservoir controller and electronic processor may be physically integrated into one assembly.

In use, the microenvironment parameters of adjacent bones of the knee may be controlled with the knee replacement components 70 of FIG. 7. After the femur, tibia, and/or patella have been prepared/cut, the components 70 are positioned against the joint bones such that the sensors 14, heating/cooling units 18, and delivery ports 16 are adjacent a cut surface of the bone. The components 70 may be secured to the bones with fasteners. The fasteners may lock mechanically in the bone and/or may thermally bond to the bone and rod. Examples of mechanical and thermal fasteners are disclosed in the thermoplastic implant documents already incorporated by reference.

With the knee components 70 implanted, the microclimate may be controlled to create an enhanced healing environment. For example, a sensor 14 may measure a microenvironment parameter and based on predetermined levels, the electronic processor 38 may instruct the reservoir controller 42 to release a substance from the reservoir. Substances which may be beneficial to a fractured bone may include bone morphogenetic proteins, antibiotics, hydroxyapitate, and other bone healing agents. The electronic processor 38 may also instruct a heating/cooling unit 18 to change the temperature of the body region. Controlling the microenvironment may be performed automatically by microprocessors based on preset parameter levels and input signals from the sensors. The microenvironment may alternatively, or additionally, be controlled by a physician via remote control. The physician may use RF, microwave, or IR energy to transmit instructions to the microprocessors in the knee components.

Figure 8A:
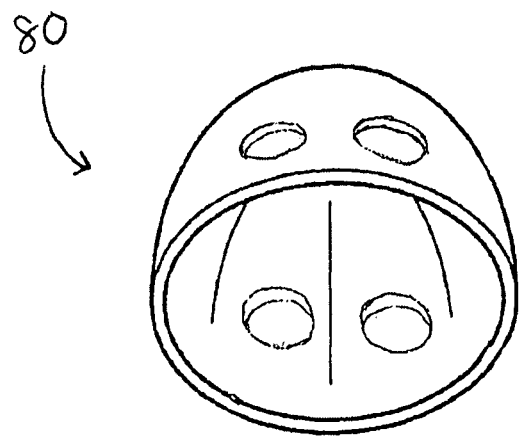
FIGS. 8A and 8B show an acetabular implant configured to control the microenvironment of a joint area.
Figure 8B:
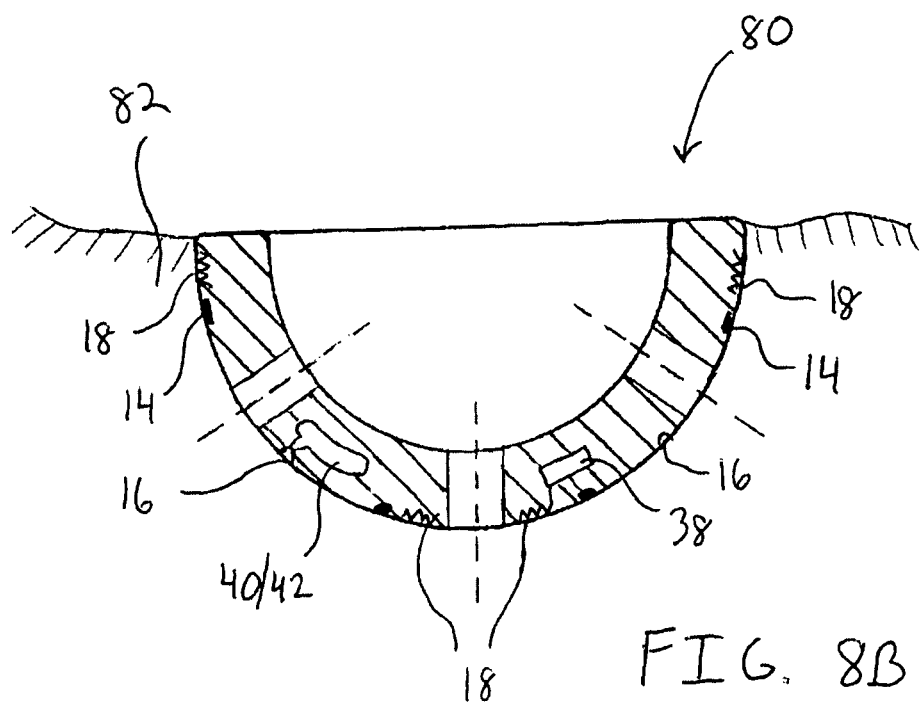

Referring now to FIGS. 8A and 8B, a hip implant 80 may include microenvironment-controlling devices. An acetabular implant 80 is generally a half-spherical socket apparatus dimensioned to receive a ball joint of the femur or femoral implant. The acetabular/ball joint implant 80 may be made of metallic, ceramic, composite, polymeric, or thermoplastic material. Other materials and structural characteristics for acetabular component are disclosed in U.S. Provisional Application No. 60/810,080 filed Jun. 1, 2006, which is hereby incorporated by reference. The acetabular implant and/or ball joint implant 80 may include sensors 14, heating/cooling units 18, and an electronic controller 38. The sensors 14 may be temperature sensors, pH sensors, moisture sensors, oxygen sensors, carbon dioxide sensors, or other sensors to measure microenvironment characteristics. The heating/cooling units 18 may be resistive heaters, an ultrasonic heaters, IR heaters, RF heaters, microwave heaters, or convection/conduction cooling devices. Both the sensors 14 and heating/cooling units 18 are controlled by the electronic controller 38, either automatically based on predetermined measurements or manually via remote control. Manual control on the implanted electronic processor may be achieved through IR or RF energy or through an implanted wire.

The hip implants 80 of the present invention may also include delivery ports 16, a reservoir(s) 40, and a reservoir controller 42. Each delivery port 16 is in fluid communication with the reservoir 40 via piping 44. The delivery ports 16 and reservoir 40 are configured for delivering a liquid, gas, gel, and/or solid to affect the microenvironment of the hip region. The substance(s) administered through the delivery ports may be any of the substances disclosed herein. The reservoir controller 42 manipulates the release rate and release period of the substance(s) in the reservoir. The reservoir controller 42 and electronic processor 38 may be linked together to function as a single system. That is, the reservoir controller and electronic processor work together to control the microenvironment of the body region. Alternatively, the reservoir controller and electronic processor may be physically integrated into one assembly.

In use, the microenvironment of adjacent hip bones 82 may be controlled with the hip implant components 80 of FIGS. 8A and 8B. After the femur and/or hip bone 82 have been prepared/cut, the component(s) 80 are positioned against the joint bones 82 such that the sensors 14, heating/cooling units 18, and delivery ports 16 are adjacent a cut surface of the bone. The component(s) 80 may be secured to the bones with fasteners. The fasteners may lock mechanically in the bone and/or may thermally bond to the bone and rod.

With the acetabular/ball joint component(s) 80 implanted, the microclimate may be controlled to create an optimal healing environment. For example, a sensor 14 may measure a microenvironment parameter and based on predetermined levels, the electronic processor 38 may instruct the reservoir controller 42 to release a substance from the reservoir 40. Substances which may be beneficial to a fractured bone may include bone morphogenetic proteins, antibiotics, hydroxyapitate, and other bone healing agents. The electronic processor 38 may also instruct a heating/cooling unit 18 to change the temperature of the body region. Controlling the microenvironment may be performed automatically by microprocessors based on preset parameter levels and input signals from the sensors. The microenvironment may alternatively, or additionally, be controlled by a physician via remote control. The physician may use RF, microwave, or IR energy to transmit instructions to the microprocessors in the hip implants.

Figure 9:
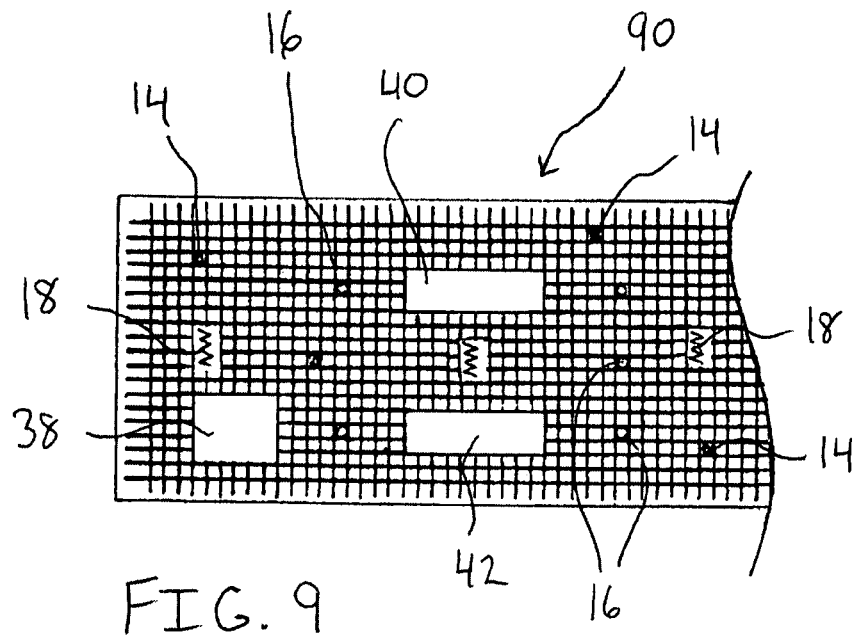
FIG. 9 is a top view of a mesh sheet having integral, microenvironment-controlling means.
Figure 10:
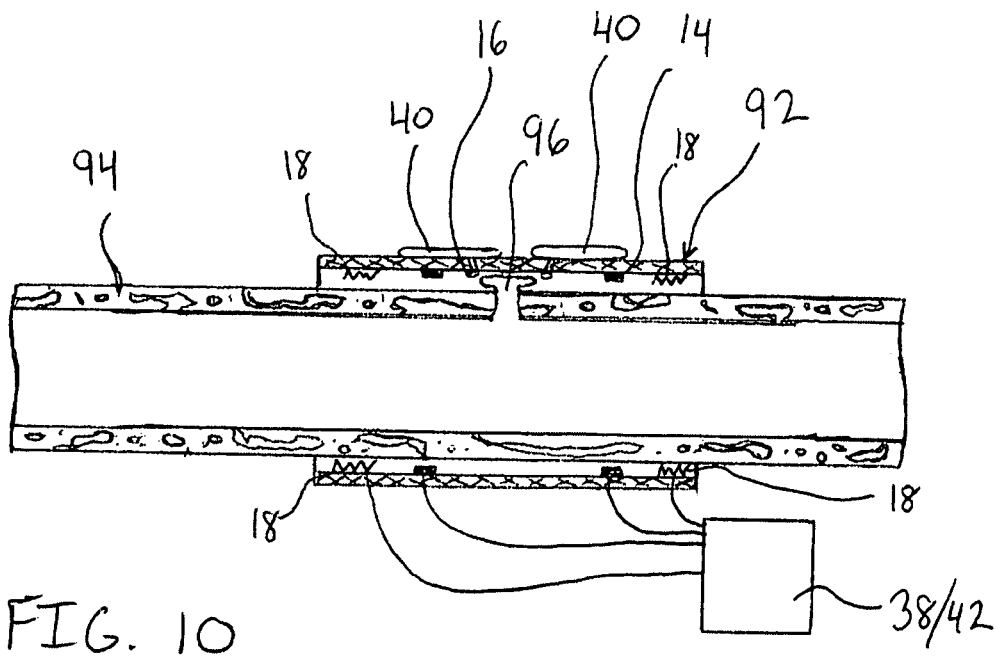
FIG. 10 is a cross sectional view of a tubular mesh constructed for controlling the microenvironment of a vessel.

In FIGS. 9 and 10, a sheet-like implant 90 is configured for controlling the microenvironment of tissue. The sheet 90 of FIG. 9 includes integrated devices for controlling microenvironment parameters, while the sheet 92 of FIG. 10 includes externally mounted devices. The sheets of FIGS. 9 and 10 may include a permeable mesh-like structure or may include an impermeable structure. The sheets 90 and 92 may be made of metallic, ceramic, composite, polymeric, or thermoplastic material. Other materials, structural characteristics, and methods of manufacture/use for sheets are disclosed in U.S. Provisional Application 60/810,080 filed Jun. 1, 2006, which was previously incorporated by reference. The sheets of FIGS. 9 and 10 may include sensors 14, heating/cooling units 18, and an electronic controller 38. The sensors 14 may be temperature sensors, pH sensors, moisture sensors, oxygen sensors, carbon dioxide sensors, or other sensors to measure microenvironment characteristics. The heating/cooling units 18 may be resistive heaters, an ultrasonic heaters, IR heaters, RF heaters, microwave heaters, or convection/conduction cooling devices. Both the sensors 14 and heating/cooling units 18 are controlled by the electronic controller 38, either automatically based on predetermined measurements or manually via remote control. Manual control on the implanted electronic processor may be achieved through IR or RF energy or through an implanted wire.

The sheets 90 and 92 may also include delivery ports 16, a reservoir 40, and a reservoir controller 42. Each delivery port 16 is in fluid communication with the reservoir 40 by way of piping 44. The delivery ports 16 and reservoir 40 are configured for delivering a liquid, gas, gel, and/or solid to affect the microenvironment of the region. The substance administered through the delivery ports 16 may be any of the substances disclosed herein. The reservoir controller 42 manipulates the release rate and release period of the substance(s) in the reservoir 40. The reservoir controller 42 and electronic processor 38 may be linked together to function as a single system. That is, the reservoir controller and electronic processor work together to control the microenvironment of the body region. Alternatively, the reservoir controller and electronic processor may be physically integrated into one assembly.

In use, the microenvironment of tissue may be controlled with the sheets of FIGS. 9 and 10. As shown in FIG. 10, a sheet 92 is wrapped around a body conduit 94 such that the sensors 14, heating/cooling units 18, and delivery ports 16 are adjacent the tissue of the conduit. The conduit 94 may be a vessel, an intestine, an esophagus, or other tubular body part. The microenvironment-controlling sheet 90 and 92 of the present invention may be used to treat diseased blood vessels. In FIG. 10, a blood vessel 94 is illustrated with an aneurysm 96 therein. The sheet 92 may be secured to the conduit with fasteners, and/or the sheet may be fastened to itself to hold the sheet around the conduit 94. A sheet with thermoplastic material may be heated to shrink wrap the sheet to the body conduit. Further disclosure on heat shrink implants may be found in U.S. Provisional Application No. 60/810,080 filed Jun. 1, 2006 which was previously incorporated by reference.

With the sheet 92 of the present invention implanted, the microclimate may be controlled to enhance healing. For example, a sensor 14 may measure a microenvironment parameter and based on predetermined levels, the electronic processor 38 may instruct the reservoir controller 42 to release a beneficial agent or substance from the reservoir 40. The electronic processor 38 may also instruct a heating/cooling unit 18 to change the temperature of the body region. Controlling the microenvironment may be performed automatically by microprocessors based on preset parameter levels and input signals from the sensors. The microenvironment may alternatively, or additionally, be controlled by a physician via remote control. The physician may use RF, microwave, or IR energy to transmit instructions to the microprocessors in the sheets.

Magnetism/Charged Particles

Figure 11:
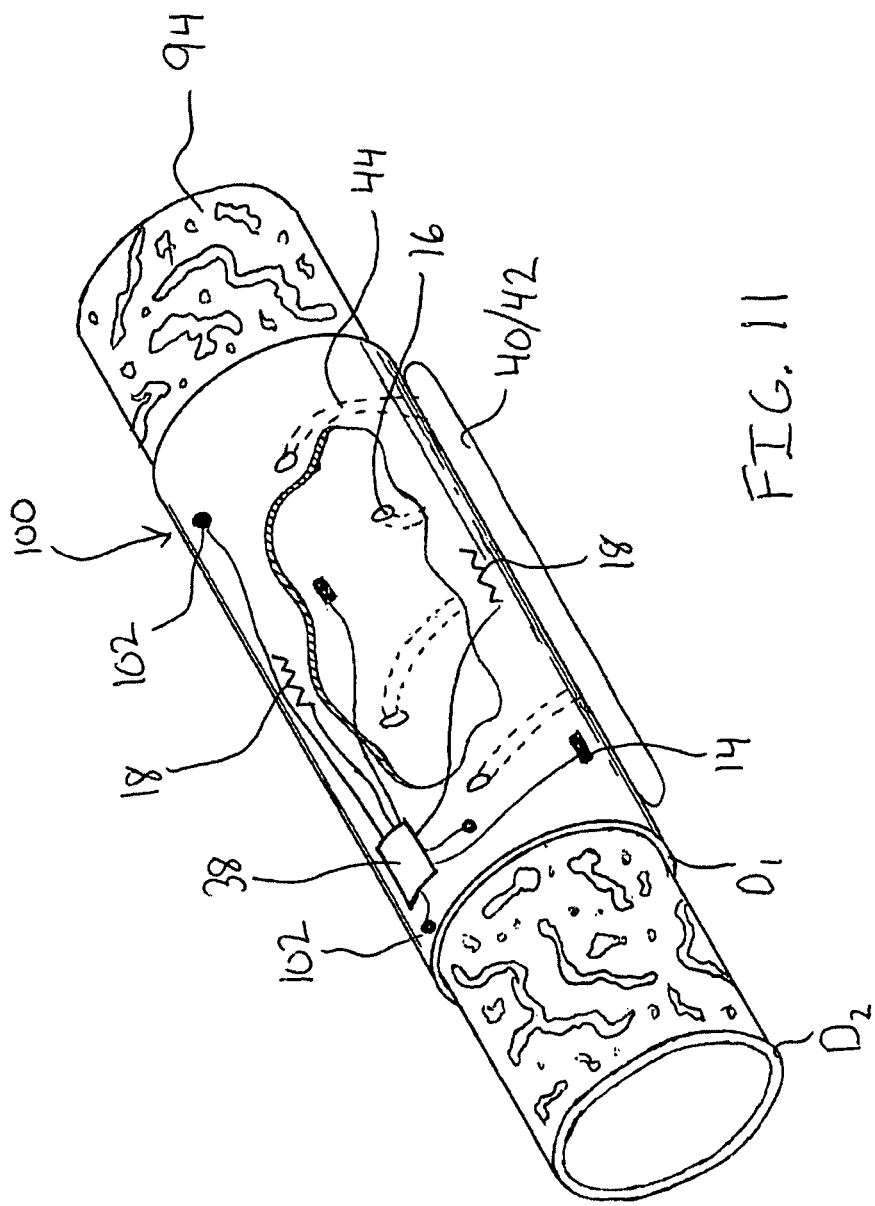
FIG. 11 is a partial cut away view of an implant designed to control the microenvironment of a blood vessel.

In addition to the microenvironment-controlling devices described with respect to FIG. 10, the implant 100 of FIG. 11 may include magnets and/or electromagnets 102. The magnets 102 attract magnetically charged particles from adjacent tissue, such as particles in blood. It is contemplated that any of the apparatus and methods disclosed herein may include and use magnets and electromagnets. Other magnet/charged particle systems are disclosed in U.S. Pat. No. 6,820,614 entitled "Tracheal Intubination" and issued Nov. 23, 2004, which is hereby incorporated by reference.

Currently, there is no practical way to concentrate a pharmaceutical agent to a local site. By charging pharmaceutical agents, cells, gene therapy agents, RNA, DNA, BMP, tissue inductive factors, etc., these substances may be concentrated at a microenvironment region by a magnet. The charged substances would flow through the blood stream until an externally mounted or internally implanted magnet draws the charged particle to a local region. The magnetic energy may also pull the changed substances from the blood stream, through the vessel wall, and into adjacent tissue.

Magnets may also be used to optimize blood flow by charging the iron ion in hemoglobin. The charged ion in hemoglobin could be concentrated at a specific local microenvironment for improved oxygen flow. Nutrient delivery, vasodilatation, vasoconstriction, cell membrane passage, cell receptor activity may also be controlled by the magnetic charge and iron molecules in the blood. Copper molecules/particles may also be charged and concentrated at a local site with magnets.

The magnets used to attract charged particles may be placed in any of the microenvironment-controlling implants disclosed herein. In addition, the nano magnets or biodegradable magnets may be integrally formed into a biodegradable polymeric or ceramic implant to form magnetic sinks. The magnets may be disposed in polylactic acid or PEEK, for example, and implanted in the body adjacent damaged tissue. The magnets may be fragments of cobalt or samarium encapsulated by a polymer. A magnetometer may be used to monitor and control the magnetic field of the sink. Increasing or decreasing the magnetic field, either internally with a microprocessor and battery or externally with an external energy source, would control the blood flow of the vessel and/or concentrate therapeutic agents in the microenvironment region. The magnetic field may be pulsed to compensate or represent heart pulses. Using a heart beat sensor, the magnetic field pulses may be synchronized based on the heart rate.

Generally, the implant 100 of FIG. 11 may be cylindrical or tubular in shape to fit around a body conduit 94 such as a blood vessel. The inner diameter $D_1$ of the cylindrical implant 100 may be less than the outer diameter $D_2$ of the conduit 94 so that fluid flowing through the conduit it is inherently accelerated at the region of the implant. The accelerated flow of the fluid allows an increased amount of therapeutic agents to be delivery through the conduit wall and into the fluid stream. This characteristic is analogous to the Bernoulli's principle: flowing fluid accelerates at a region of decreased area/volume.

Cylindrical Implant

The implant 100 of FIG. 11 may be made of metallic, ceramic, composite, polymeric, or thermoplastic material. The cylindrical implant 100 may include sensors 14, heating/cooling units 18, magnets 102, and an electronic controller 38. The sensors 14 may be temperature sensors, pH sensors, moisture sensors, oxygen sensors, carbon dioxide sensors, or other sensors to measure microenvironment characteristics. The heating/cooling units 18 may be resistive heaters, ultrasonic heaters, IR heaters, RF heaters, microwave heaters, or convection/conduction cooling devices. The magnets 102 may be earth magnets or electromagnets. The sensors 14, heating/cooling units 18, and magnets 102 are controlled by the electronic controller 38, either automatically based on predetermined measurements or manually via remote control. Manual control on the implanted electronic processor may be achieved through IR or RF energy or through an implanted wire.

The cylindrical implant 100 may also include port holes 16, a reservoir(s) 40, a reservoir controller 42, and a suction means, such as an electric or manual pump. The port hole 16 may be in fluid communication with the reservoir 40 by way of piping 44. The port hole 16 and reservoir 40 are configured for delivering a liquid, gas, gel, and/or solid to affect the microenvironment of the region. The substance(s) administered through the delivery ports 16 may be any of the substances disclosed herein. The reservoir controller 42 manipulates the release rate and release period of the substance(s) in the reservoir. The reservoir controller 42 and electronic processor 38 may be linked together to function as a single system. That is, the reservoir controller and electronic processor work together to control the microenvironment of the body region. Alternatively, the reservoir controller and electronic processor may be physically integrated into one assembly.

A port hole 16 may instead, or in addition to, be connected to the suction means. The suction at the port hole would create a negative pressure (Venturi effect) on the surrounding tissue. The suction could increase blood flow by vasodilatation or draw blood away from a certain tissue area causing vasoconstriction. The negative pressure may also aid in the delivery and/or concentration of pharmaceutical substances. It is contemplated that the other embodiments of the present invention may also include suction port holes, a suction pump, and associated tubing. For example, the knee replacement components 70 of FIG. 7 may include port holes and a suction pump. This could improve vascular flow of knee tissue. The pump could be integrated into the implant such that as the knee is moved back and forth suction is created.

In use, the microenvironment of tissue may be controlled with the cylindrical implant 100. As shown in FIG. 11, the implant 100 is positioned around a body conduit 94 such that the sensors 14, heating/cooling units 18, magnets 102, and delivery ports 16 are adjacent the tissue of the conduit. The conduit 94 may be a vessel, an intestine, an esophagus, or other tubular body part. For the sake of drawing simplicity, the inner diameter of the implant is generally the same as the outer diameter of the conduit. However, as previously described, a smaller inner diameter of the implant would create increased fluid flow thereby increasing the administration rate of therapeutic agents. The microenvironment-controlling implant 100 of FIG. 11 may be used to treat diseased blood vessels or other body lumens. The implant 100 may be secured to the conduit with fasteners and/or, the implant may be fastened to itself to hold the implant around the conduit. A cylindrical implant with thermoplastic material may be heated to shrink wrap the implant to the body conduit. Further disclosure on heat shrink implants may be found in patent document already incorporated by reference.

With the cylindrical implant 100 of the present invention positioned, the microclimate may be controlled to create an optimal medical climate. For example, a sensor 14 may measure a microenvironment parameter and based on predetermined levels, the electronic processor 38 may instruct the reservoir controller 42 to release a substance from the reservoir 40. The electronic processor 38 may also instruct a heating/cooling unit 18 to change the temperature of the body region and/or instruct the magnets 102 to energize thereby drawing charged particles to the conduit wall. The diameter of the cylindrical implant 100 may be increased or decreased with the electronic processor 38 and the heating/cooling units 18. Heating the implant may expand the implant diameter and cooling the implant may decrease the diameter, or vice versa. Controlling the microenvironment may be performed automatically by microprocessors based on preset parameter levels and input signals from the sensors. The microenvironment may alternatively, or additionally, be controlled by a physician via remote control. The physician may use RF, microwave, or IR energy to transmit instructions to the microprocessors in the implant.

It is contemplated that other known surgical implants may include the microenvironment-controlling devices described herein. For example, the present invention provides a microenvironment-controlling stent; cannula; catheter; spinal rod, plate, or pin; face and head reconstruction implant; shoulder replacement component; elbow replacement implant; hand and foot implant, and other similar implants.

Climate Controlled Surgery

In addition to the apparatus previously described to control the microenvironment of a living body, the present invention provides methods and apparatus for performing climate-controlled surgery. During a surgical procedure, the body region being operated on is exposed to the operating room environment. This is especially relevant during maximally invasive procedures but also relevant during minimally invasive surgery, endoscopic surgery, and insufflation. Usually, the operating room is dry, and tissue response is affected by desiccation. The room temperature often varies between 60 and 65 degrees Fahrenheit, and the local tissue is cooled significantly. Also, when tissue is cut it releases enzymes which change the local pH. Bleeding changes the local pH as well. Irrigation is often used at the surgical region, but the irrigation is not isotonic to decrease osmolarity and drug tension. Moreover, coolness and change in pressure effect vascular flow, causing vasoconstriction, therefore, fewer nutrients enter the wound site and less oxygen is delivered to the site which can further damage the tissue.

Using climate-controlled surgery, the local body temperature, not just the core body temperature, may be regulated. Desiccation may be minimized, and vascular flow may be maintained. Also, oxygen tension and nutrient delivery may be optimized. The local pH level may be controlled, and tissue osmolarity may be maintained.

Although a limited number of examples are provided herein, it is contemplated that any type of surgery may be combined with the climate-controlling methods herein. For example, the present invention may be applied to surgery of the foot and ankle, hand and wrist, elbow, knee, hip, shoulder, genitalia, head, etc. As will become clearer subsequently, surgery on a region of an extremity is most conducive for the methods of climate-controlled surgery.

Figure 12:
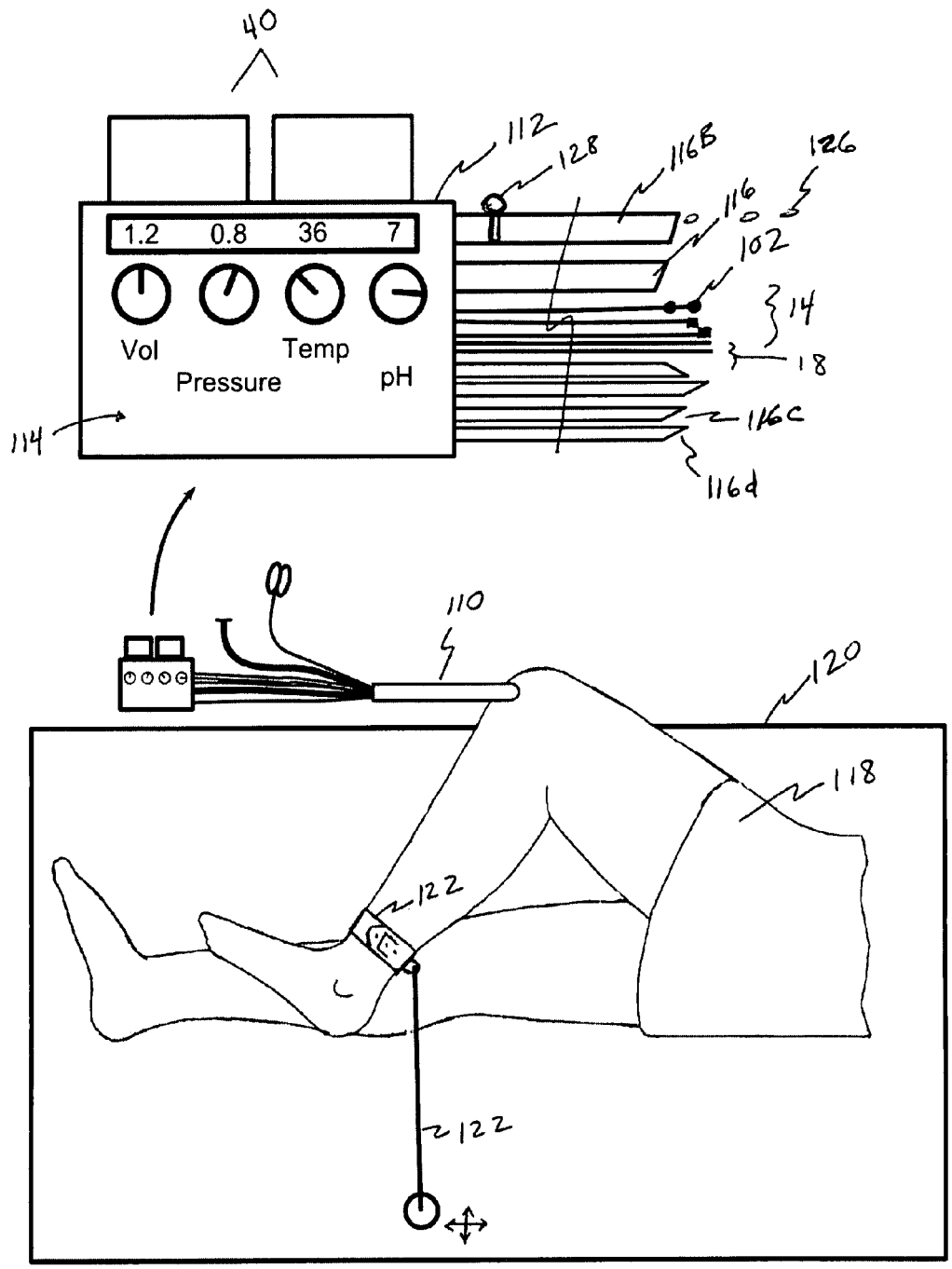
FIG. 12 shows apparatus for controlling the microenvironment of a joint during joint replacement surgery.

Referring now to FIG. 12, a system for climate-controlled knee surgery is illustrated. The surgical system includes a hollow structure, such as an expanding cannula, or trocar 110, a microprocessor controller 112, sensors 14, heating/cooling units 18, magnets 102, reservoirs 40, pumps 114 and related fluid conduit 116. The trocar 110 is dimensioned to enter the body region of the patient that is to be operated on. The sensors 14 may be temperature sensors, pH sensors, moisture sensors, oxygen sensors, carbon dioxide sensors, or other sensors to measure microenvironment characteristics. The heating/cooling units 18 may be resistive heaters, an ultrasonic heaters, IR heaters, RF heaters, microwave heaters, or convection/conduction cooling devices. The magnets 102 may be earth magnets or electromagnets. The sensors 14, heating/cooling units 18, magnets 102, reservoirs 40, and pumps 114 are controlled by the electronic controller 112, either automatically based on predetermined measurements or manually via remote control. Manual control on the implanted electronic processor may be achieved through wire or wireless remote control. Wireless control may be performed with IR, RF, or microwave energy.

To perform climate-controlled knee surgery, a patient 118 may be placed in the prone position with the patient's leg to be operated on positioned adjacent an edge of the support table 120. A leg cuff and strap 122 may be connected with the patient's foot or ankle. The strap 122 may be connected with an attachment point which may be movable up/down, left/right, or forward/backward.

Sensors 14 and/or magnets 102 may be attached to the patient's tissue in or around the incision area, positioned through trocar 110, or adjacent to the entry area. The sensors 14 and magnets 102 may be connected to the controller via wires or wireless IR or RF energy. Fluid, such as saline, water, plasma, or other biocompatible fluid may be added to the trocar 110 through the inlet pipe 116 via the pump 114. Alternatively, for insufflation, a gas may be added to trocar 110. The heating/cooling unit 18 may vary the temperature of the fluid during filling and throughout the surgical procedure. Based on signals from the sensors 14 and/or on the physician's direction, pharmaceutical or therapeutic agents stored in the reservoirs 40 may be selectively released into the fluid stream. The combination of agent reservoirs 40, heating/cooling units 18, sensors 14, magnets 102, pumps 114, and fluid 126 forms a means for creating, maintaining, and changing the environment of the surgical region. During and after the operation, the fluid 126 may be extracted from the submersion tank 110 via the outlet pipe 116*b* and valve 128. The valve 128 may be controlled by the microprocessor controller and/or by the physician (shown).

One of reservoir 40 may advantageously contain a substance which may be used to control pH. It is advantageous to use a calcium based substance due to a potentially beneficial effect on bones, although a wide variety of substances may be used, as described above. The pH controlling substance may be a gas, liquid, or powder, and may enter the surgical field through a pipe 116*c* and be collected through a separate pipe 116*d*. Adjustment of pH and temperature may advantageously be carried out to reduce postoperative pain.

Pump Implant

The present invention also provides an implantable pump for controlling the microenvironment of a body region. The pump may control the microenvironment parameters such as temperature, pH level, moisture, humidity, oxygen tension, carbon dioxide tension, rate of blood flow, nutrient-content, and the presence of pharmaceutical agents. Through the use of pumps, reservoirs, sensors, and controllers, these parameters may be measured, changed, and monitored, externally or internally.

In an exemplary embodiment, a pump system would control the local regulation of pH. pH-changing agents could be placed in an implantable pump which may be externally or internally controlled. The pump/reservoir may include pH controlling agents such as calcium carbonate or calcium sulfate. The pump could have valves which release the agents to the local circulation, or it could have an osmotic membrane covering, another type of salt such as sodium chloride, potassium chloride, calcium carbonate, calcium sulfate. Calcium based compounds may be used because they are easily metabolized by the body and can help with issues of osteoporosis. Some salts, because of their ability to bind to proteins, may also be efficacious with pH control. The pH control system could also be ionic anionic. Certain salts that are released may have an affinity to bind to proteins and affect the local microclimate.

Alternatively, a body region may be made more acidic. This can be accomplished, for example, be delivering carbon dioxide (or a liquid carbon dioxide) to tissue. As this agent is released it would create carbonic acid which could make the pH more acidic. The pH level may be automatically or manually controlled with sensors and a microprocessor. The sensors positioned locally in the tissue could detect the pH level and could turn on and off the delivery of a pH-changing agent. The pH level could be varied during the course of the day, or during a time when one wants improved tissue effect.

Stomach Irritator

Figure 13:
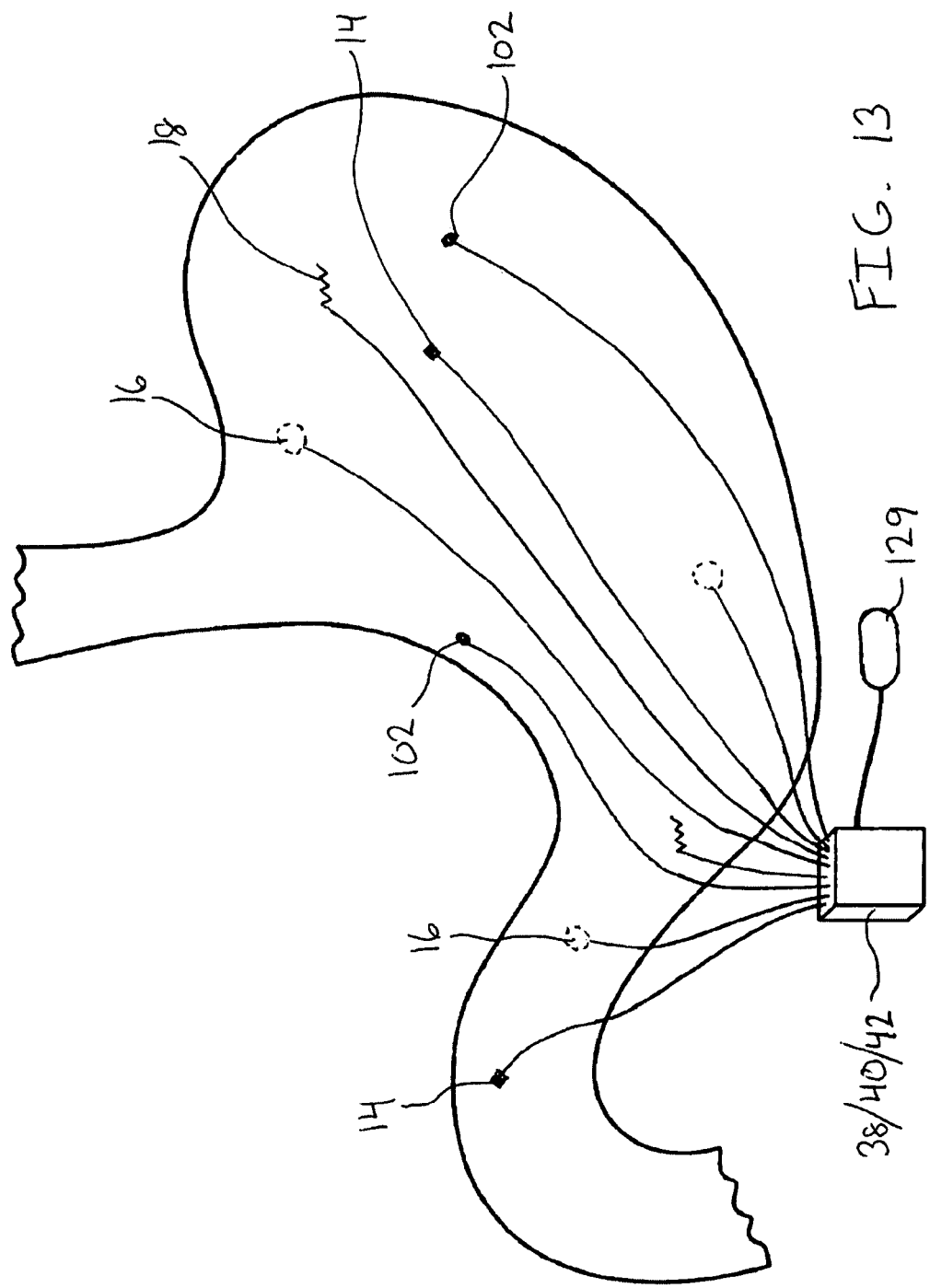
FIG. 13 illustrates devices connected with a stomach for controlling the microenvironment thereof and thereby controlling the appetite of the person.

In a more specific embodiment, the pump system may be used as a stomach irritator. The pump system may be used for irritable bowel and bladder problems as well. The stomach irritator could be used in place of or in addition to gastric bypass surgery. The irritator could be a pH irritator or electromagnetic irritator. An electromagnetic irritator may include electromagnets and a microprocessor for delivering magnetic energy to the stomach thereby decreasing the patient's appetite. The pH irritator system could create nausea by releasing viral agents or irritating agents to the stomach which would cause stomach muscle spasm and therefore decrease the patient's interest or desire to eat. The system illustrated in FIG. 13 may include an electronic controller 38, sensors 14, magnets 102, heating/cooling units 18, delivery ports 16, a reservoir 40, a battery 129, and related wire and conduit. These components may be made of a biodegradable material. The batteries may be recharged with tissue flow, tissue movement, heat changes, thermal changes, or pH changes. Other electrical generators and battery recharging devices and methods are described subsequently.

The irritator systems could be used as a temporary obesity treatment. The systems could be implanted transcutaneously, percutaneously, endoscopically, and/or minimally invasively. The implanted systems may be fastened in place with thermoplastic bands, stapling, and/or ultrasonic welding techniques described in patent documents incorporated herein. The irritator systems of the present invention do not operate by reducing the volume of the stomach, rather the systems function like arrhythmia of the heart where an arrhythmia pattern in the stomach wall musculature is created. This arrhythmia then inhibits normal mechanical operation of the stomach, and contributes to a feeling of bloatedness or fullness. The system may affect one or more locations of the stomach, it would thus be diffuse affect, similar to creating gastric fibrillation. As previously described, the system may function electrically or electromagnetically. It may also function ultrasonically where an ultrasonic generator transmits vibratory energy to the stomach. Furthermore, the system may function thermally using heating units described herein to create irritation-type spasm in the stomach.

In addition to the pH irritator and electromagnet irritator, the present invention provides a metallic ion irritator. This system may include metallic ions to conduct temperatures of the stomach, bowel, bladder, etc. The metallic ions may be percutaneously implanted and activated with an electrical transmitter which may be external to the body, battery operated, and wearable by the patient. Thus, the patient or physician may control the temperature of the stomach, etc. by changing the signal of the transmitter.

Microenvironment Controlled Surgery of the Eye

Figure 14:
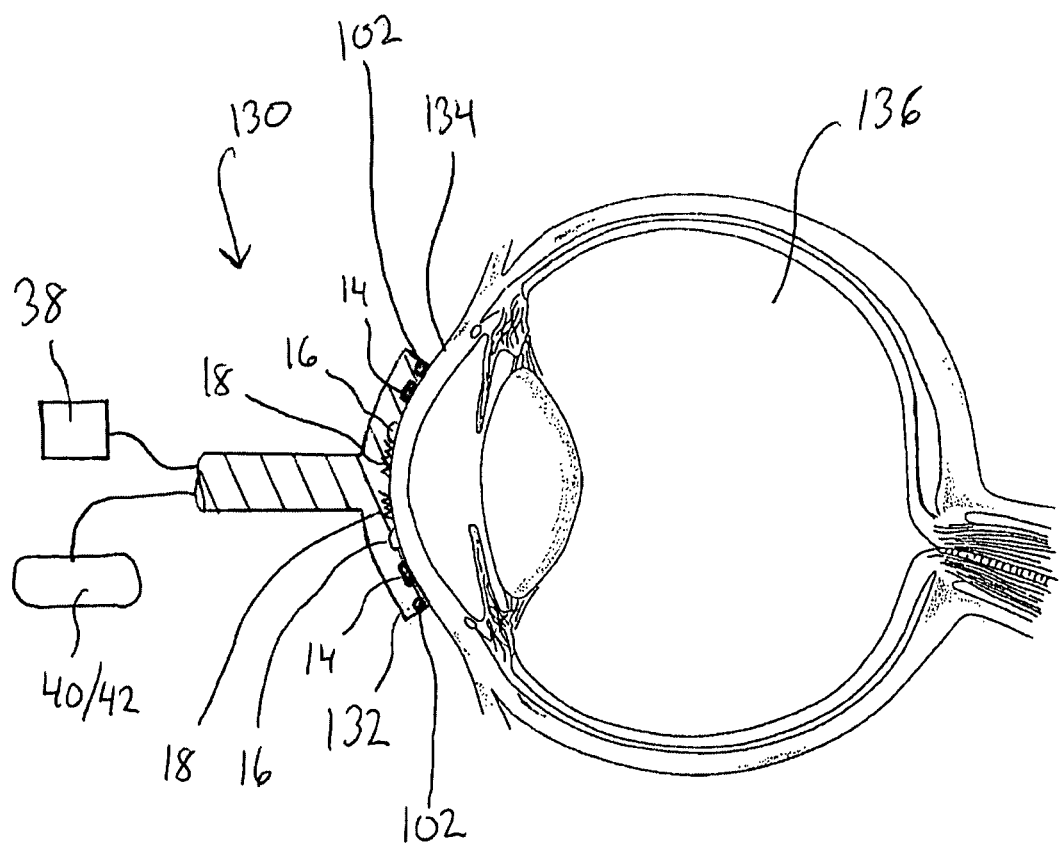
FIG. 14 is a cross sectional view of a device for correcting vision defects of an eye.

Another embodiment of microenvironment-controlling surgery is illustrated in FIG. 14. The microenvironment-controlling devices of the present invention may be used to correct vision of the eye. The surgical apparatus 130 includes a concave body 132, sensors 14, heating/cooling units 18, delivery ports 16, reservoirs 40, and a microprocessor controller 38. The concave body 132 may be made of metallic, ceramic, or polymeric material. In a specific embodiment, the concave body 132 is an ultrasonic end effector capable of producing vibratory energy. The sensors 14 may be temperature sensors, pH sensors, moisture sensors, oxygen sensors, carbon dioxide sensors, or other sensors to measure microenvironment characteristics. The heating/cooling units 18 may be resistive heaters, an ultrasonic heaters, IR heaters, RF heaters, microwave heaters, or convection/conduction cooling devices. The sensors 14, heating/cooling units 18, and end effector (concave body) 132 may be controlled by the electronic controller 38, either automatically based on predetermined measurements or manually via remote control.

The apparatus of FIG. 14 also includes port holes 16, a reservoir(s) 40, a reservoir controller 42, and a suction means, such as an electric or manual pump. The port hole 16 may be in fluid communication with the reservoir 40 by way of piping 44. The port hole 16 and reservoir 40 are configured for delivering a liquid, gas, gel, and/or solid to affect the microenvironment of the region. The substance(s) administered through the delivery ports 16 may be any of the substances disclosed herein. The reservoir controller manipulates the release rate and release period of the substance(s) in the reservoir 40. The reservoir controller 42 and electronic processor 38 may be linked together to function as a single system. That is, the reservoir controller and electronic processor work together to control the microenvironment of the body region. Alternatively, the reservoir controller and electronic processor may be physically integrated into one assembly.

A port hole 16 may instead, or in addition to, be connected to the suction means. The suction at the port hole 16 would create a negative pressure (Venturi effect) on the surrounding cornea tissue 134. The negative pressure may aid in the delivery and/or concentration of pharmaceutical substances.

The microenvironment of the cornea 134 may be controlled during vision correction surgery with the apparatus 130 of FIG. 14 by the following method. Initially, a physician will measure the uncorrected shape of the patient's cornea 134 and determine the amount and location of reshaping necessary to improve vision in the eye 136. With the calculations completed, the concave body 132 may be place in contact with the cornea 134. Using the body 132 as an ultrasonic horn, vibration energy may be emitted to raise the temperature of the cornea 134 and reshape the outer surface. Before, during, and after reshaping, pharmaceutical agents may be delivered to the cornea via the port openings 16, piping, and reservoir 40. The port openings 16 may also provide suction to the cornea 134 to draw the pharmaceutical agents to a specific location or depth of the cornea. The sensors 14 may measure any of the microenvironment parameters, such as temperature, acidity, etc. and provide the measurements to the electronic controller. The heating/cooling units 18 may be used to change the temperature of the cornea to optimize the reshaping and healing processes. Moreover, magnets 102 as described in early embodiments may be used to control the microenvironment parameters of the cornea as well. All the microenvironment-controlling devices (sensors, units, port openings, magnets, reservoir, etc.) may be automatically controlled by the microprocessor, manually controlled by the physician, or a combination of manual and automatic control.

Transdermal or Topical Delivery

Certain embodiments described thus far have been microenvironment-controlling implants or surgical procedures. The embodiments of FIGS. 15, 16, 17A, and 17B provide microenvironment-controlling apparatus which are positioned against skin. A topical pharmaceutical delivery system may administer drugs locally and transcutaneously and/or percutaneously. The system uses poloxamer lecithin organogel (PLO), lecithin isopropyl palmitate, polypropylene glycol, ethyl propylene glycol, ethoxydiglycol, and/or liposomal components to help dissolve or transport pharmaceutical agents through the skin. While lecithin is a preferred substance, ketoprofen, licocaine, and steroids in concentrations of about 20 percent may also be resorbed through the skin.

Generally, as therapeutic agents are delivered topically, the diffusion coefficient remains the same thereby releasing an agent at a constant rate. Physicians, however, may prefer that some pharmaceutical agents be topically administered at different rates depending on the need of the patient or desire of the physician. The microenvironment-controlling devices of the present invention may be used to selectively delivery topical agents at various rates and periods. Raising the temperature or pH level, for example, may increase the diffusion coefficient, while cooling the skin or lowering the pH level may slow drug delivery. Suction applied to the skin may also vary the drug flow rate. The negative pressure would create a Venturi effect in the skin which would enhance penetration through the skin and into an adjacent artery or vein. For example, a topical delivery system may be placed on the hand to concentrate drug administration over the radial artery.

The types of pharmaceutical substances which may be delivered topically are well known in the art. These substances may be combined by the manufacturer in the factory or by the physician in the hospital/operating room to create a specific mixture, or cocktail of drugs that meet the patient's needs. These cocktails may be placed or incorporated into a gelatin, biologic foam, or biodegradable foam to absorb through the skin and into the body. One type of gelatin which may be used is pluronic gel. Pluronic gel or any other carrier may be combined with steroids, thrombolytic agents, pain relieving agents, opioids, lidocaine, anti-inflammatory agents, or chemotherapeutic agents for controlled topical local administration. Other pharmaceutical agents disclosed herein may be used with the topical system as well.

It is contemplated that the topical delivery system of the present invention may be combined with electroshock wave energy, RF energy, and electromagnetic energy.

Figure 15:
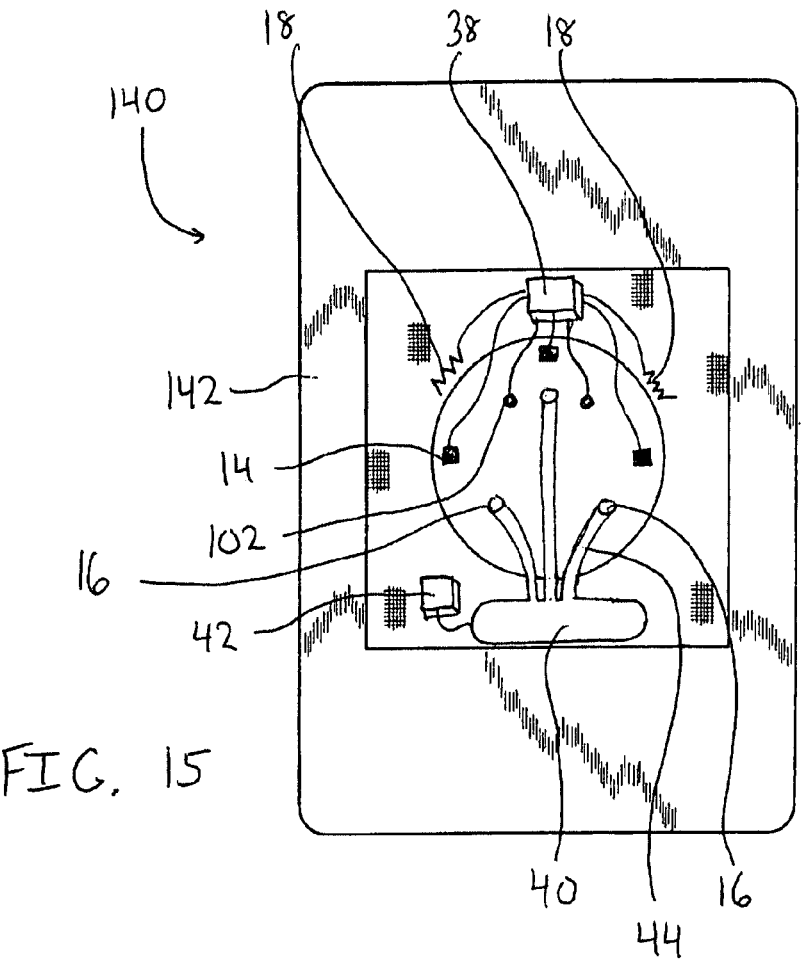
FIG. 15 shows a tissue patch having microenvironment-controlling devices.

A topical pharmaceutical delivery patch 140 is illustrated in FIG. 15. The patch 140 may include a base sheet 142, sensors 14, heating/cooling units 18, magnets 102, and microprocessor controllers 38. The base sheet 142 may be similar to known patches such as the nicotine patch or birth control patch. The sheet 142 may include an adhesive on the skin facing surface. The sensors 14 may be temperature sensors, pH sensors, moisture sensors, oxygen sensors, carbon dioxide sensors, or other sensors to measure microenvironment characteristics. The heating/cooling units 18 may be resistive heaters, an ultrasonic heaters, IR heaters, RF heaters, microwave heaters, or convection/conduction cooling devices. The magnets 102 may be earth magnets or electromagnets. The sensors 14, heating/cooling units 18, and magnets 102 are controlled by the electronic controller 38, either automatically based on predetermined measurements or manually via remote control. Manual control of the electronic processor may be achieved through IR or RF energy or through an implanted wire.

The topical delivery system may also include port holes 16, a reservoir(s) 40, a reservoir controller 42, and a suction means, such as an electric or manual pump. The port hole 16 may be in fluid communication with the reservoir by way of piping 44. The port hole 16 and reservoir 40 are configured for delivering a liquid, gas, gel, and/or solid to affect the microenvironment of the region. The substance(s) administered through the delivery ports 16 may be any of the substances disclosed herein. The reservoir controller 42 manipulates the release rate and release period of the substance(s) in the reservoir. The reservoir controller 42 and electronic processor 38 may be linked together to function as a single system. That is, the reservoir controller and electronic processor work together to control the microenvironment of the body region. Alternatively, the reservoir controller and electronic processor may be physically integrated into one assembly.

A port hole 16 may instead, or in addition to, be connected to the suction means. The suction at the port hole 16 would create a negative pressure on the surrounding tissue. The suction could increase blood flow by vasodilatation or draw blood away from a certain tissue area cause vasoconstriction. The negative pressure may also aid in the delivery and/or concentration of pharmaceutical/therapeutic substances.

In an exemplary method of use, the patch of FIG. 15 may control the microenvironment of soft tissue, such as skin. The patch 140 is positioned against the skin such that the sensors 14, heating/cooling units 18, magnets 102, and delivery ports 16 are adjacent the tissue. The patch 140 may be secured to the skin with adhesive. With the patch positioned, the microclimate may be controlled to create an optimal topical drug delivery. For example, a sensor 14 may measure a microenvironment parameter and based on predetermined levels, the electronic processor 38 may instruct the reservoir controller 42 to release a substance from the reservoir 40. The electronic processor 38 may also instruct a heating/cooling unit 18 to change the temperature of the body region, instruct the magnets 102 to energize thereby drawing charged particles to the skin, and/or instruct increased or decreased flow rate of the therapeutic agent. Controlling the microenvironment may be performed automatically by microprocessors based on preset parameter levels and input signals from the sensors. The microenvironment may alternatively, or additionally, be controlled by a physician via remote control. The physician may use RF, microwave, or IR energy to transmit instructions to the microprocessors in the implant.

Ultrasonic Topical Drug Delivery

Figure 16:
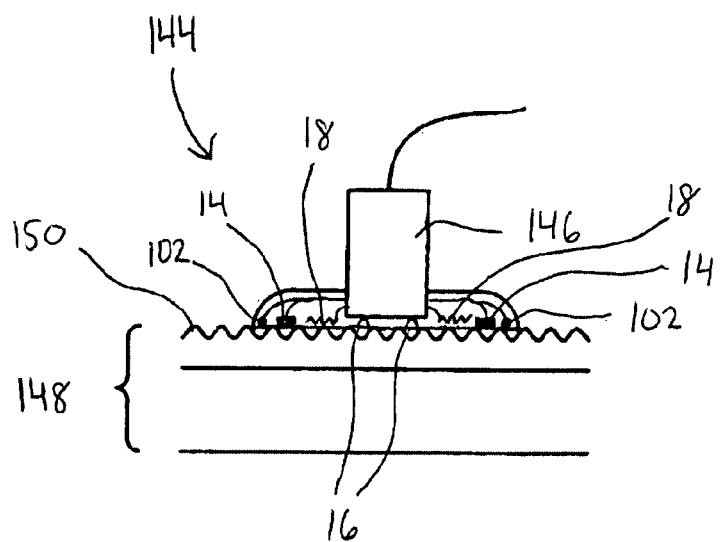
FIG. 16 illustrates a device for controlling the microenvironment of skin.

Referring now to FIG. 16, an ultrasonic topical drug delivery system 144 may control the microenvironment of soft tissue. The ultrasonic system 144 may include a main body 146, sensors 14, heating/cooling units 18, delivery ports 16, reservoirs 40, and a microprocessor controller 38. In a specific embodiment, the body 146 is an ultrasonic end effector capable of producing vibratory energy. The sensors 14 may be temperature sensors, pH sensors, moisture sensors, oxygen sensors, carbon dioxide sensors, or other sensors to measure microenvironment characteristics. The heating/cooling units 18 may be resistive heaters, an ultrasonic heaters, IR heaters, RF heaters, microwave heaters, or convection/conduction cooling devices. The sensors 14, heating/cooling units 18, and end effector (concave body) 146 may be controlled by the electronic controller 38, either automatically based on predetermined measurements or manually via remote control.

The ultrasonic topical system 144 also includes port holes 16, a reservoir(s) 40, a reservoir controller 42, and a suction means, such as an electric or manual pump. The port hole 16 may be in fluid communication with the reservoir 40 by way of piping. The port hole 16 and reservoir 40 are configured for delivering a liquid, gas, gel, and/or solid to affect the microenvironment of the region. The substance(s) administered through the delivery ports may be any of the substances disclosed herein. The reservoir controller 42 manipulates the release rate and release period of the substance(s) in the reservoir. The reservoir controller 42 and electronic processor 38 may be linked together to function as a single system. That is, the reservoir controller and electronic processor work together to control the microenvironment of the body region. Alternatively, the reservoir controller and electronic processor may be physically integrated into one assembly.

A port hole 16 may instead, or in addition to, be connected to the suction means. The suction at the port hole 16 would create a negative pressure (Venturi effect) on the surrounding tissue 148. The negative pressure may aid in the delivery and/or concentration of pharmaceutical substances.

The microenvironment of skin may be controlled during topical administration of a pharmaceutical substance. In use, the ultrasonic drug delivery system 144 of FIG. 16 may be positioned against soft tissue, such as skin 148. To administer a pharmaceutical agent 150 to the skin 148, the operator/physician may utilize any of the microenvironment-controlling devices. For example, the end effector 146 may transmit vibratory energy to the skin 148, and the heat/cooling units 18 may change the temperature of the skin. A substance 150 may be delivered from the reservoir via the port openings 16. The substance 150 may be any of the agents disclosed herein, such as a pH-changing agent. The port openings 16 may alternatively, or additionally, provide negative pressure to the skin. The magnets 102 of the system may attract changed particles to the skin for drug concentration. All of these microenvironment-controlling devices permit the microenvironment parameters to be measured, changed, and monitored. A microprocessor may automatically control the devices, or a physician may control the devices and parameters manually.

Blood Loss

It is contemplated that the apparatus and methods of FIGS. 15 and 16 may further be used to stop bleeding. The systems may deliver individual drugs or drug cocktails to the bleeding tissue while changing and monitoring the microenvironment parameters. Examples of substances the systems may used to control bleeding include epinephrine, sucrose products as a vasoconstrictor, tetracycline to increase or decrease scarring, and soluble gels.

Iontophoresis

Controlling the microenvironment of tissue may also be combined with iontophoresis, a form of electro-osmosis. Currently, physical therapists are using iontophoresis to help penetrate cortisone into the skin. An electric charge is placed between electrodes positioned adjacent the skin. The electric current aids in topical drug administration. This technique may be combined with devices and methods for controlling the microenvironment parameters of a region of the body. Along with the electric current, the temperature (ultrasound), pH level, moisture, humidity, porosity, pressure, and other parameters may be changed and monitored. Instead of having a constant current, the electric charge may be oscillated, pulsed, or alternated during topical drug delivery, and instead of using iontophoresis for applying therapeutic agents to the skin, the technique may be used for intracorporal drug delivery to other tissue, such as bone, muscle, and cartilage, as well.

Any of the pharmaceutical agents disclosed herein may be combined with iontophoresis techniques. In addition, certain cellular elements such as DNA, RNA, BMPs, protein, hormones, fetal cells, or other cellular elements may be included in a tissue scaffold or tissue graft which may be implanted and iontophoretically delivered. The cellular elements may be driven into tissue, like bone matrix, with or without an implantable scaffold or graft. The system could be a closed system left inside the body where electrical energy is used to drive cells, such as mesenchymal or stem cells, or other therapeutic agents into tissue. Alternatively, the system may be positioned partially outside the body with only the electrodes and microenvironment-controlling devices implanted.

Figure 17A:
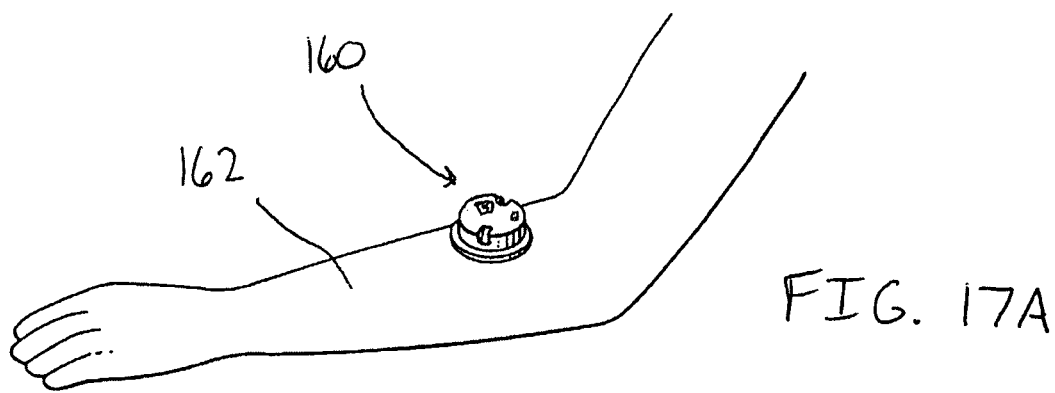
FIGS. 17A and 17B show an apparatus for iontophoretic treatment of tissue.
Figure 17B:
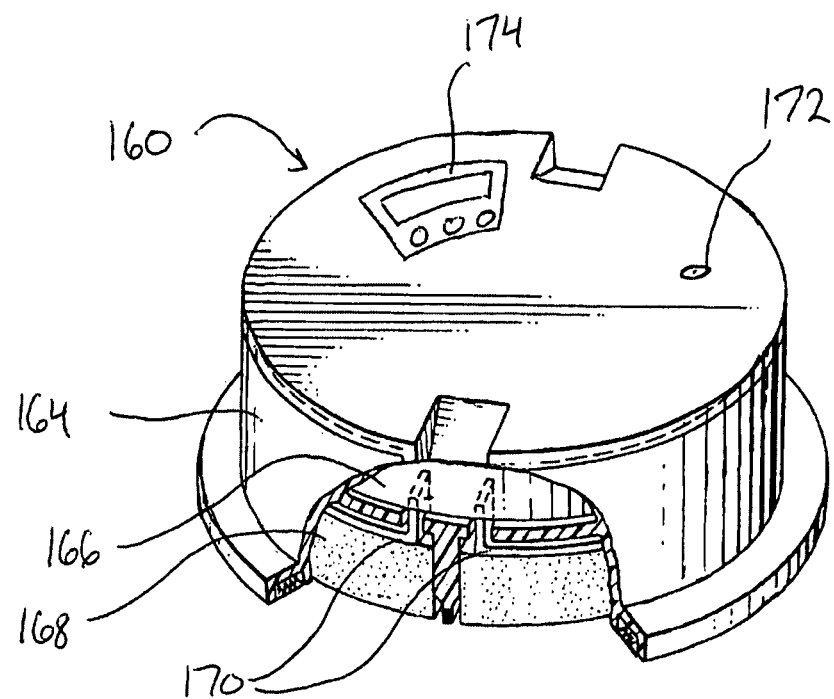

FIGS. 17A and 17B illustrate an exemplary embodiment of an iontophoretic system. In FIG. 17A, a device 160 for iontophoretic treatment is shown positioned on the surface of a patient's skin 162. As previously described, the iontophoretic device 160 of the present invention may be fully or partially implanted for delivery of therapeutic agents intracorporeally. The device 160, as illustrated in FIG. 17B, includes a cylindrical body 164 made of a biocompatible material, such as metal or plastic. Electrical components such as a microprocessor and power supply are located in an upper compartment 166, while reservoirs are positioned in a lower compartment 168 of the body 164. Between the upper and lower compartments is a pair of iontophoretic electrodes 170, typically of electrically conductive silicone/carbon material, and which are separated from each other by a divider baffle. The electrodes 170 are connected to the electrical components. A power recharge port or reservoir refill port 172 may be located on the cylindrical body 164. Operation of the iontophoretic device 160 may be via a control station 174 which includes a screen and selector buttons. For an implantable iontophoretic device, operation may be through RF, microwave, or IR energy.

The iontophoretic device of FIGS. 17A and 17B may include means for controlling all the microenvironment parameters. Also, it is contemplated that the implants and methods previously disclosed for controlling the microenvironment of the body region may also include an iontophoretic drug delivery system.

Dementia

Microenvironment control may further be used to prevent or treat dementias. Currently, it is believed that Alzheimer's disease may be related to decreased temperature and decreased blood flow to the brain. Existing pharmaceuticals such as Aricept may increase blood flow slightly. Other studies suggest possible cognitive function, walking exercises, or reading exercises may improve overall cognitive function. The present invention provides control of the microclimate of the brain, specifically vascular flow, temperature, and other factors such as pH, electrical stimulation, electromagnetic, etc. This relates to diurnal curve. The temperature or blood flow would not be constant, but would be controlled regularly. This could be related to the cortisone levels in the body or could be a diurnal control where it might be warmest at certain parts of the day and cooler, but could potentially track the patient's normal temperature curves, being lowest at 8:00 AM and highest at 8:00 PM. It could also match serum cortisol levels. The microenvironment parameters may be changed or given multiple spikes during the course of the day. Normally, there is not a constant increase in temperature; rather, it could fluctuate or vary. Controlling the temperature could also be combined with physical exercises or cognitive function exercises.

One objective of microenvironment control is to increase the temperature/blood flow to the brain. This could be done by mechanical, electrical, or thermal devices for the head, neck, or for the carotid vasculature, for example. This may be performed with 1) electrical control—a heating/cooling unit could be ultrasound, RF, electromagnetic, fluid controlled, convention or conduction cooling, etc.; 2) mechanical control—a hat or a turtleneck neck warmer could be used to warm the blood flow to the brain, and it could be made of a material which allows pharmaceuticals to be delivered transcutaneously (Venturi effect); 3) technique control—the location and timing of heating/cooling units could affect the temperature curves; 4) cognitive features—an active brain undergoing an activity, learning, study tools, activity tools, which would also essentially increase temperature, blood flow, but in combination with the blood flow curves; and 5) pharmaceutical treatments which would improve vascular flow, vasodilatation—vasodilators such as nitroglycerin or transcutaneous medication may be transcutaneously delivered over the carotid arteries through a Venturi type effect.

The reverse could also occur in children that may be, for example, hyperactive or patients that are having seizures. These conditions may be controlled by performing exactly the opposite: cooling and decreasing the blood flow selectively, or decreasing the overall core temperature of the brain or selective locations with the brain. This could be done externally, internally, transcutaneously, percutaneously, etc.

In addition to dementias and hyperactivity, it is contemplated that other diseases or disorders such as sleep apnea, hypothermia, and arthritis may be prevented or treated by controlling the microenvironment parameters.

Body Suit/Worn Items

Figure 18:
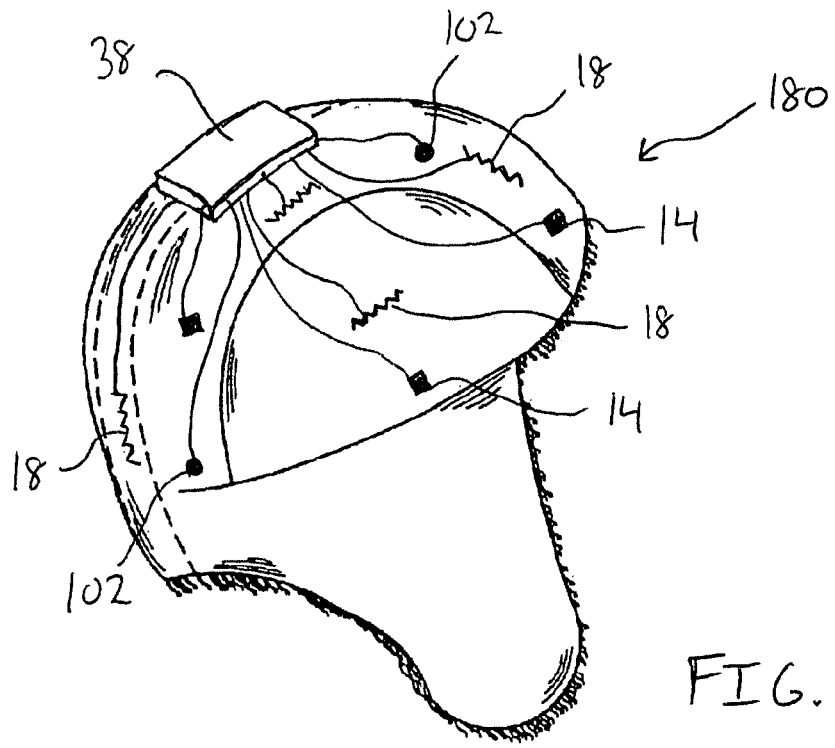
FIG. 18 is a perspective view of a hat for controlling microenvironments of the head.
Figure 19:
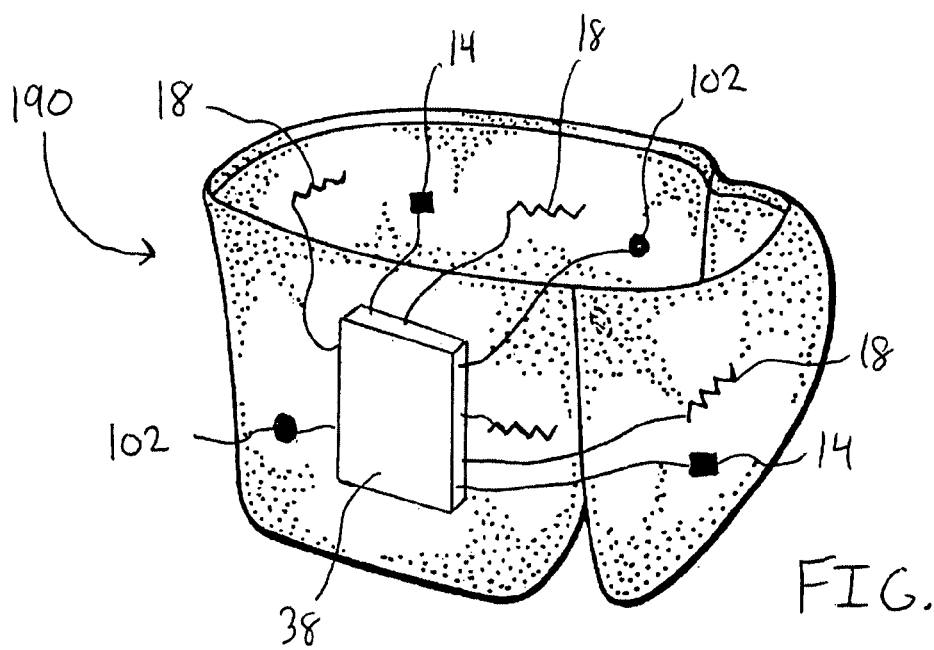
FIG. 19 is a perspective view of a collar for controlling microenvironments of the neck.

FIGS. 18-21 illustrate various, non-limiting, embodiments of microenvironment-controlling outerwear. A cap 180 is shown in FIG. 18, while a neck scarf 190 is illustrated in FIG. 19. The cap 180 covers the patient's head from the orbital ridge to the base of the skull medially and from the ventral aspect of the head down laterally to the base of the skull below the ears. The scarf 190 wraps around the patient's neck. By altering the head/neck temperature with the cap/scarf, vasoconstriction or vasodilatation would decrease or increase blood flow. The cap 180/scarf 190 includes a microprocessor 38 and a plurality of sensors 14, magnets 102, and heating/cooling units 18. The sensors 14 may be temperature sensors, pH sensors, moisture sensors, oxygen sensors, carbon dioxide sensors, or other sensors to measure microenvironment characteristics. The heating/cooling units 18 may be resistive heaters, an ultrasonic heaters, IR heaters, RF heaters, microwave heaters, or convection/conduction cooling devices. The magnets 102 may be earth magnets or electromagnets. The magnets 102 may be used to alter blood flow and increase circulation. The cap 180 may also include ear cannel inserts to monitor core temperature and balance the temperature with a heating/cooling unit in the cap. The sensors 14, heating/cooling units 18, inserts, and magnets 102 are controlled by the microprocessor controller, either automatically based on predetermined measurements or manually via remote control.

Figure 20:
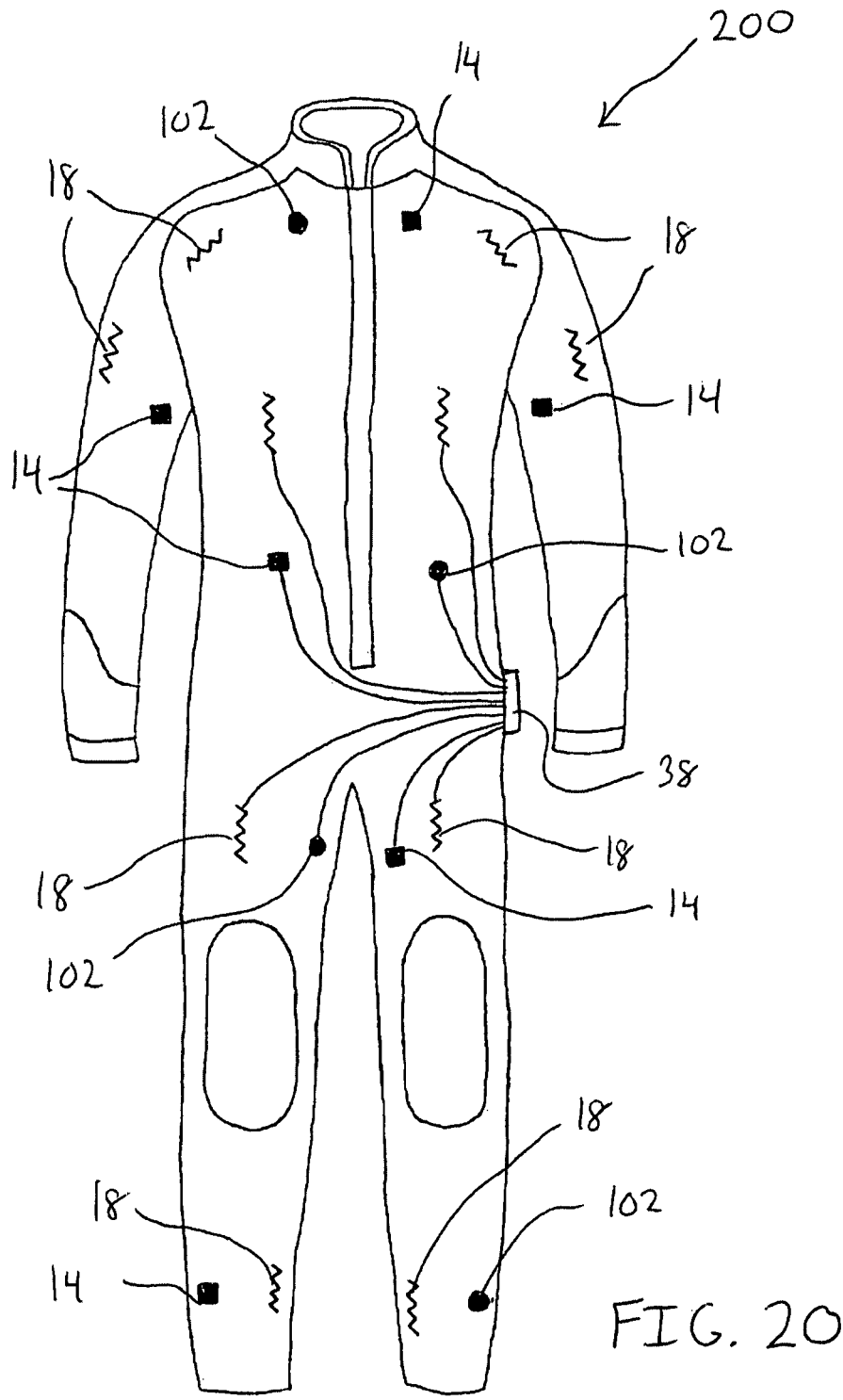
FIG. 20 is a front view of a suit for controlling one or more microenvironments of the human body.
Figure 21:
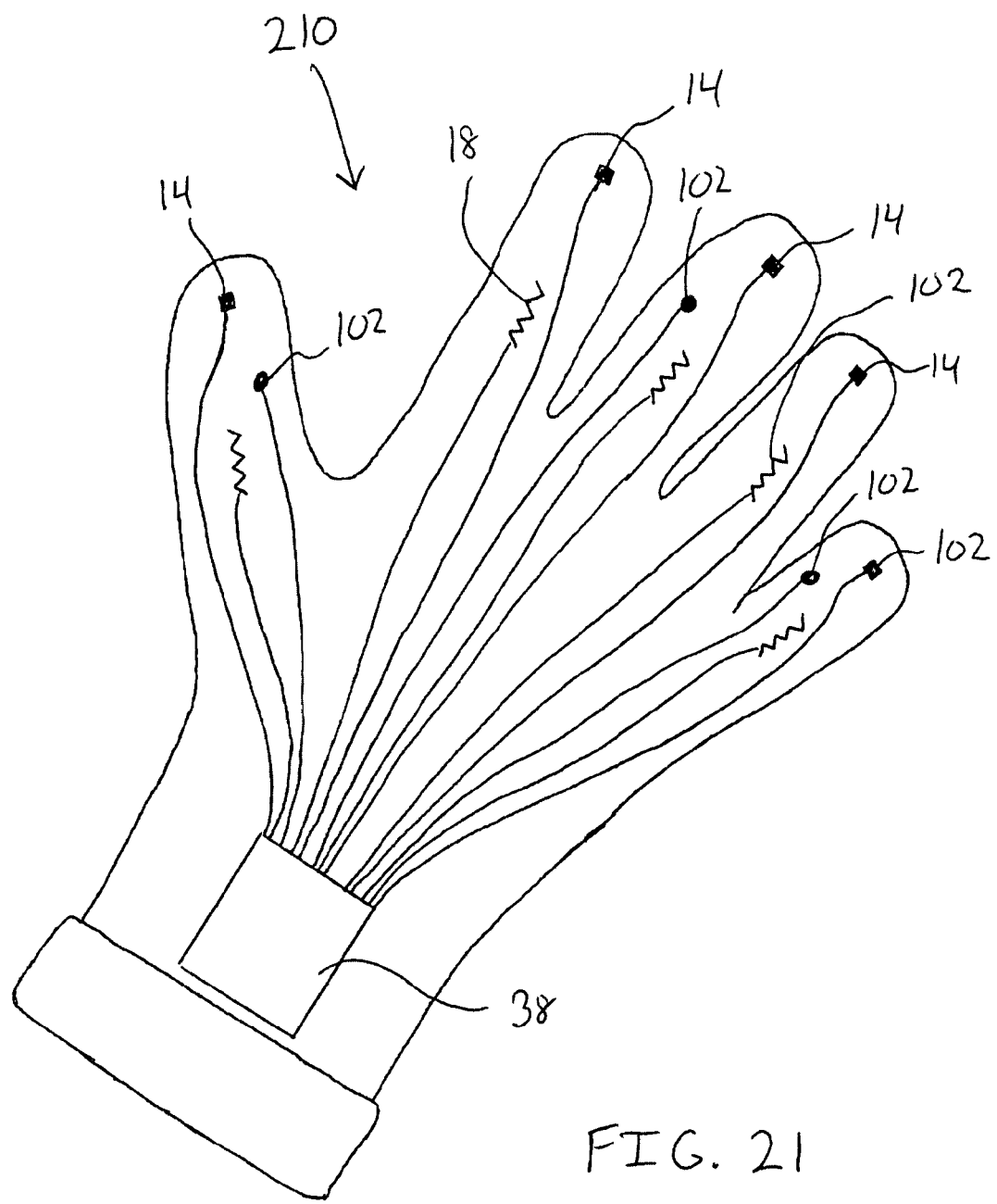
FIG. 21 shows a glove for controlling microenvironments of the hand.

A microenvironment-controlling body suit 200 is shown in FIG. 20, and a glove 210 is illustrated in FIG. 21. The suit 200 covers the patient's torso, arms, and legs. The glove 210 is configured to cover the patient's hand and wrist. By altering the temperature with the suit/glove, vasoconstriction or vasodilatation would decrease or increase blood flow. The suit 200/glove 210 includes a microprocessor 38 and a plurality of sensors 14, magnets 102, and heating/cooling units 18. The sensors 14 may be temperature sensors, pH sensors, moisture sensors, oxygen sensors, carbon dioxide sensors, or other sensors to measure microenvironment characteristics. The heating/cooling units 18 may be resistive heaters, an ultrasonic heaters, IR heaters, RF heaters, microwave heaters, or convection/conduction cooling devices. The magnets 102 may be earth magnets or electromagnets. The magnets 102 may be used to alter blood flow and increase circulation. The sensors 14, heating/cooling units 18, inserts, and magnets 102 are controlled by the microprocessor controller 38, either automatically based on predetermined measurements or manually via remote control.

Therapeutic Bacteria

In a related aspect of the invention, bacteria may be used to control the microenvironment. The previously described reservoirs associated with microenvironment-controlling devices may further include bacteria for changing microenvironment parameters. Alternatively, or additionally, bacteria may be placed in a mesh-like sac, with or without other therapeutic agents. In an exemplary embodiment, bacteria which are easily tolerated or symbiotic with the body, such as normal flora, may be seeded in tissue to control, for example, the pH level. Some toxic bacteria which require controlling in the body include staph aureus or methicillin resistant staph aureus (MRSA). If a patient has an infection with MRSA, a physician may want to affect the pH level by varying the level during the course of the day. Implanted bacteria may also control local blood flow, oxygen tension, and other microenvironment parameters.

In another exemplary embodiment, certain types of e-coli may be very well tolerated by the body, and not toxic, or have been made less viable. There are also various bacteroides and bactericides which are well tolerated. These could be used to displace staph aureus in the right pH environment. Therefore, physicians could use therapeutic bacteria to fight off dangerous bacteria. The therapeutic bacteria being normally tolerated by the body could then be killed off, removed, or if the microclimate changes the therapeutic bacteria could be eradicated. It is contemplated that physicians could do the same with other types of symbiotic organisms, different types of parasites or saprophytes, as well as different types of viral approaches to fighting off an infection by seeding the tissue with another infection and controlling the microenvironment parameters, such as pH level, oxygen tension, temperature, etc. Once the acute infection or the more severe infection is resolved then the physician can more easily manage the local infection.

To help further describe the use of bacteria to fight diseases, an analogy is provided with respect to the processing of sausage. During manufacture, sausage is dry cured giving it a different smell and different flavor. During this process, bacteria which produces lactic acid act as a fermenting agent. The bacteria add to the flavor, but they also have preservative properties. The acid and other compounds kill off other bacteria that spoil food. This same principle may be applied to killing off unwanted bacteria causing caustic infections in the body, as previously described. The use of bacteria or other targeting substance may be combined with control of the microenvironment parameters. The bacteria in sausage are lactobacillus casei. These bacteria are able to function in very low oxygen tensions, high salt concentrations, and low oxygen conditions. A physician could induce these conditions locally to fight off local infections then change the oxygen tension to ultimately kill off the lactobacillus. Lactobacillus is a facultative anaerobe and could be delivered transcutaneous, percutaneously, etc. to the infection site of the patient.

Wicking Agent

The therapeutic bacteria, or any pharmaceutical agent, may also place in a reservoir located in a biodegradable screw or hollow biodegradable object. The implant could have a wicking action which could wick the bacteria/agent over to another material such as a scaffold or collagen. Wicking action includes capillary action, capillarity, or capillary motion. For example, periapatite or hydroxyapatite could be wicked through or around the exterior surface of an implant, allowing for an increased distribution area. The wicking agent may be a porous ceramic, polymer, composite, or fabric. It may be biodegradable and flexible. In an exemplary embodiment, a biodegradable porous site may be attached to a periapatite acetabular shell so BMP, antibiotics, or other agents may be delivered over the entire surface of the shell by simply allowing it to wick from a hollow biodegradable implant or reservoir.

It is contemplated that the wicking means for delivering a therapeutic agent may be combined with the other microenvironment-controlling devices described herein. That is, in addition to sensors, magnets, reservoirs, and heating/cooling units, a wicking agent may be used to deliver therapeutic agent to control the microenvironment. The wicking action may be controlled automatically by the microprocessor controller of the implant and/or manually by a physician via remote control or RF, IR, microwave energy. Wicking control includes methods described elsewhere herein, and including ports, closable portals, retractable or movable wicking material, and movable seals.

Implantable Filter

In another related aspect, the present invention provides implantable filters and methods of their use. The implantable filter may be positioned in the body to capture cellular material, proteins, enzymes, or other body substances. A fistula may be created between two body parts such as two organs, and a filter may be positioned in the fistula to gather body substances. For example, a blood filter may be placed in the vasculature or a side channel of a blood vessel which selectively traps white cells and immunoglobulins. The filter may be implanted for a short period of time, i.e. minutes (during an operation), or could be left in place for a longer period of time (between surgical procedures). The filter could be a porous collagen filter, a porous polylactic acid, a PGA compound, or other known filter material. When sufficient substance has been captured, the filter may be removed, for example percutaneously, and re-implanted in infected tissue or where healthy tissue cells are needed.

An implantable filter may also be placed in a joint or synovial site to harvest cartilage cells. The filter may be connected with a tissue scaffold. The scaffold could be left floating in the joint, and while the joint moves, cells or slough from the joint surface may be captured in the filter. These captured cells could then be implanted into a joint defect or in a different joint to repair surface defects. The scaffold and cells may be used in combination with pressed or shaped bone or bone-like products, such as OP-1. In an exemplary use, the scaffold/cells may be osteoinductive and/or cartilage inductive to resurface a joint. In addition, the scaffold/cells may be sculpted or molded in situ or in the operating room and fastened in place with different types of thermal bonding agents, adhesives, polysaccharides, etc.

In another embodiment, the joint filter (and scaffold) may be affixed to the joint tissue. Movement of the knee joint would allow cells to populate this membrane to allow healing of cartilage lesions/biologic resurfacing. Implantation of the joint filter may be performed with computer navigation and imaging technology. The joint tissue may be contoured to form fit the scaffold/filter. To fasten the filter to tissue, it may be tissue welded with biocompatible temperatures and molded to the surface of the bone such as with ultrasonic welding. For example, the filter may conform to the articular surface so that it would have a smooth contour with the biologic or biodegradable filter or membrane attached.

To induce cells into the filter, body movement may be used to create a hydraulic effect or Venturi effect. Alternatively, or additionally, the membrane or filter could have a suction type pump that could be built into it which would create negative pressure, either constantly or at variable times during the course of the day. This could be internally or externally controlled. The suction would deliver or pull cells into the center of the filter/membrane/matrix to populate cells in a three dimensional portion of the matrix. The suction could be delivered with a pump, electrically or electromagnetically. To determine when the filter has been sufficiently populated, a physician could use ultrasound energy, density determination, MRI, CT scan, or other similar volumetric measuring methods.

An implantable filter may also be placed in bone marrow. As the bone marrow moves, either naturally or through external pressure/suction, stem cells could be selectively harvested through the filter. The filter and cells may be removed from the bone marrow during the same procedure or during another surgical procedure. The filter and/or stem cells may then be implanted at the local tissue site (i.e. heart, brain, spinal cord, or other organ). In an exemplary embodiment, the filter is percutaneously implanted in bone marrow of the hip. It could be implanted and removed during the same procedure or could be left in for a period of hours or days and then could be removed. The harvested cells and/or filter could be compressed or shaped and placed into a defect, such as a damaged heart muscle.

Cells captured with a filter of the present invention may also be used in peripheral muscle, cartilage graft, bone graft, or other implant. The cells and/or filter could further be used on the surface of joint replacement components.

In a further exemplary embodiment, a filter may be implanted in a patient's eye to collect retinal cells. The captured cells may be harvested from the filter and used to prevent or treat macular degeneration or another eye tissue injury. The harvested retinal cells along with the filter may be implant in the eye. In this configuration, the filter/cells may be used to treat macular degeneration, where the degeneration may be caused by a chlamydial infection. To do so, antibiotics, tetracycline, doxycycline, and other therapeutic agents may be placed on or impregnated in the filter. The agent(s) may be time released locally to help cool off the chlamydial infection within the eyeball/retina itself. This embodiment is particularly beneficial because antibiotics and other substances do not go through the blood brain barrier and do not get into the tissue inside the eyeball.

Various methods of use are contemplated for the cell filters of the present invention. For example, a fistula may be formed between an artery and vein, and the filter could be placed in the fistula to permanently harvest cells. The filter then could have tubing which could deliver the captured cells to another site in the body. An implanted filter could be left within bone marrow to trap cells. Then, through a closed line which could be subcutaneously implanted to another tissue location, the cells could be transported to a transplant site while maintaining the cells viable by body fluid. The simple movement of body parts, organs, blood movement, etc., would trap these cells in the filter and move the cells to the recipient site.

The filters of the present invention may include different porosity to trap different types of cells. They could have adhesives such as polysaccharide adhesives, or certain ionic or covalent attractions for certain types of cells. The filters may also be coated it with immunoglobulins or other pharmaceuticals or proteins to attract or bond certain types of white cells, red cells, or blood marrow elements.

In a further filter embodiment, an implantable filter may be positioned in the amniotic membrane, either free floating or attached to one surface of the membrane. As the fetus is moving, cells are sloughed off and will be caught by the filter/mesh. The filter/mesh could then be sent off to cell culture, be stored in a tissue bank, or be reimplanted in the same patient or another patient. The captured cells may include, for example, dedifferentiated stem cells, mesenchymal cells, embryonal cells, and fetal cells. The fetus would be untouched and would maintain its viability. The filter may be implanted and removed through an expandable cannula, under fluoroscopic visualization, or ultrasonic guidance without damaging the fetus.

Similarly, a filter of the present invention could be used to attach or grasp tissue cells on the surface of the heart. If a person has a heart attack, the victim could lose muscle cells in one portion of the heart, while another portion of the heart may remain viable. An implantable filter may be positioned in that portion of the heart that remains viable. As the heart moves, certain cardiac cells would be trapped into the filter. The filter and/or cells could then be removed at the same surgical time or during another surgical procedure. The cells may be transplanted into the area where the cardiac cells are dead to induce cardiac cell formation. These cells could be combined with bone marrow cells, OP-1, and other tissue inductive factors to enhance growth.

All of the above described filters may be placed within or on the surface of any type of tissue. The porosity, surface area, and/or contour of filter may be used to entrap or capture cells. To aid in cell collection, negative pressure, such as a sponge which would apply slow negative pressure, could be applied to the filter and surrounding area. A sponge would draw collected cells to the center of the matrix, progressively populating the entire matrix.

Figure 22:
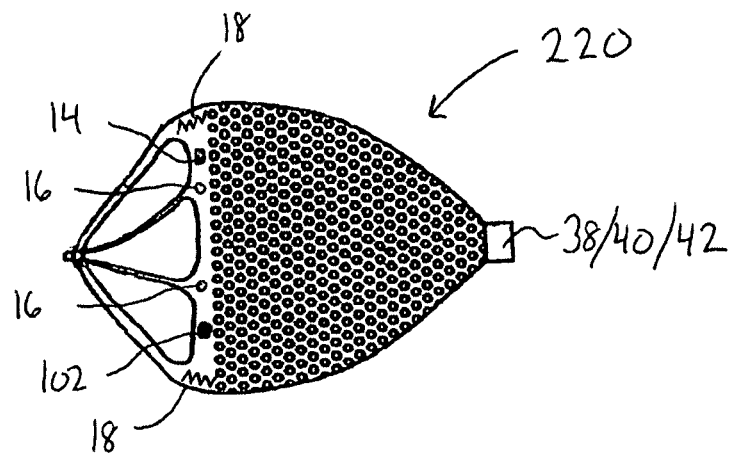
FIG. 22 shows a filter of the present invention having integrated microenvironment-controlling means.
Figure 23:
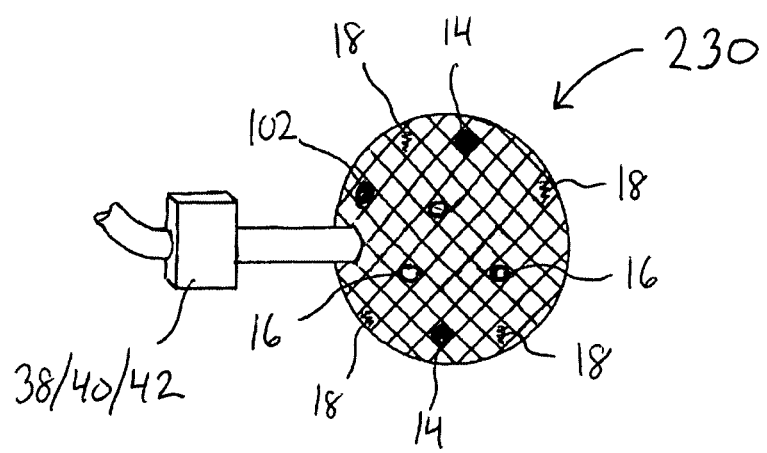
FIG. 23 illustrates another filter having an external controller.

FIGS. 22 and 23 illustrate exemplary embodiments of the filters of the present invention. In FIG. 22 the filter 220 is generally shaped like a circular parachute or sea anchor, while the filter 230 of FIG. 23 is generally flat. The filters may include metallic, ceramic, composite, polymeric, or thermoplastic material. The filters may include a mesh-like structure and may be flexible or rigid and biodegradable or biostable. The filters may include sensors 14, heating/cooling units 18, magnets 102, and an electronic controller 38. The sensors 14 may be temperature sensors, pH sensors, moisture sensors, oxygen sensors, carbon dioxide sensors, or other sensors to measure microenvironment characteristics. The heating/cooling units 18 may be resistive heaters, an ultrasonic heaters, IR heaters, RF heaters, microwave heaters, or convection/conduction cooling devices. The magnets 102 may be earth magnets or electromagnets. The sensors 14, heating/cooling units 18, and magnets 102 are controlled by the electronic controller 38, either automatically based on predetermined measurements or manually via remote control. Manual control on the implanted electronic processor may be achieved through IR, RF, or microwave energy or through an implanted wire.

The filters 220/230 may also include port holes 16, a reservoir(s) 40, a reservoir controller 42, and a suction means, such as an electric or manual pump. The port hole 16 may be in fluid communication with the reservoir 40 by way of piping. The port hole 16 and reservoir 40 are configured for delivering a liquid, gas, gel, and/or solid to affect the microenvironment of the region. The substance(s) administered through the delivery ports may be any of the substances disclosed herein, including bacteria. The reservoir controller 42 manipulates the release rate and release period of the substance(s) in the reservoir. The reservoir controller 42 and electronic processor 40 may be linked together to function as a single system. That is, the reservoir controller and electronic processor work together to control the microenvironment of the body region. Alternatively, the reservoir controller and electronic processor may be physically integrated into one assembly.

A port hole 16 may instead, or in addition to, be connected to the suction means. The suction at the port hole 16 would create a negative pressure (Venturi effect) on the surrounding tissue. The suction would increase the capture rate of cells. The negative pressure may also aid in the delivery and/or concentration of pharmaceutical substances.

Methods of using the filters 220/230 of the present invention have been previously illustrated. That is, the filters may be implanted in the vasculature, bone marrow, fistula, organ, etc. to collect desired cells and other body substances. The filter 230 of FIG. 23 is particularly applicable to muscle, joint, organ, or bone repair as previously described. The filter 230 may be contoured or shape to form to the surface of tissue. With the filters implanted, the microclimate may be controlled to create an optimal cell/substance capturing climate. For example, a sensor 14 may measure a microenvironment parameter and based on predetermined levels, the electronic processor 38 may instruct the reservoir controller to release a substance from the reservoir. The electronic processor 38 may also instruct a heating/cooling unit 18 to change the temperature of the body region and/or instruct the magnets 102 to energize thereby drawing charged particles to the conduit wall. Controlling the microenvironment may be performed automatically by microprocessors based on preset parameter levels and input signals from the sensors. The microenvironment may alternatively, or additionally, be controlled by a physician via remote control. The physician may use RF, microwave, or IR energy to transmit instructions to the microprocessors in the implant.

Aerosol Delivery

In another related invention, therapeutic and pharmaceutical agents may be delivered to body tissue in a pulsed, atomized manner. The following description of a pharmaceutical agent distribution system may be used in combination with and/or integrated with the microenvironment-controlling apparatus and methods described herein. Generally, during the course of medical treatment, medicaments are administered to patients before, during, and after surgery. In many medical situations it is necessary or desirable to administer small amounts of medicaments and other pharmaceutical agents to a patient over a relatively long period of time.

For example, heparin is administered to a patient in need thereof by an intravenous "drip" procedure. Other medicines which may be administered through the "drip" process include antiarrhythmics, vitamins, hormones, corticosteroids, anesthetics and antibiotics. These medicines may be administered intermittently by bolus injection or continuously by gravity dispensers. Bolus injections may not, however, match the patient's actual requirements and may subject the patient to larger dosages of drugs than required as well as frequent needle insertion. Drug delivery through gravity dispensers may limit the patient's lifestyle by tethering the patient to the intravenous drip apparatus. Furthermore, the dispensing rate is not always constant.

Rather than relying on the manual injection of bolus doses of drugs using syringes or on manually setting the drip rate of gravity-fed intravenous infusion sets, health professionals are utilizing infusion devices that electronically or mechanically control the infusion rate of drugs as they are being administered to patients. Infusion pumps may include compact pump housings or larger stationary pump housing units. The administration of prescribed drugs has been accomplished through infusion tubing and an associated catheter or the like, thereby introducing the drug intravenously. Pain, tissue damage and post-op complications have long been tolerated as negative side effects from the use of existing hypodermic drug delivery infusion systems. The pain and tissue damage are a direct result of uncontrolled flow rate in conjunction with excessive pressures created during the administration of drug solutions within the tissue spaces. Also, it has been demonstrated that particular pressures for a specific tissue type will cause damage. It is therefore critical that a specific flow rate in conjunction with a specified pressure range be maintained during the delivery of fluids (drugs) when a subcutaneous injection is given preventing pain response as well as tissue damage.

The most common application of infusion devices is for the maintenance of appropriate fluid levels in patients. Fluid therapy is commonly used in the treatment of burns, the pre- and postoperative management of surgical patients and in the treatment of dehydration. The administration of drugs provides the greatest challenge to infusion devices. For a drug to be effective, the concentration of any drug at its site of action must be sufficiently high for the drug to be effective, yet the concentration must not be too high for the drug to become toxic to the patient.

Used in applications such as delivering anesthetics during surgery, chemotherapy for cancer, and oxytocic agents for inducing labor, continuous drug infusion reduces the fluctuations in a drug's concentration that occurs with the more traditional modes of drug administration such as injections and pills. Moreover, continuous drug infusion assures a continuous therapeutic action as long as the infusion rate is appropriate.

In contrast to continuous drug infusion pumps, some infusion pumps deliver drugs providing intermittent, episodic or limited drug delivery. An intermittent infusion pump is used to automatically administer a desired amount of liquid medicant to a patient. The liquid medicant is supplied from a reservoir and pumped into the patient via a catheter or other injection device. The manner in which the liquid is infused is controlled by the infusion pump controller, which may have various modes of infusion, such as a periodic release of medicine or a ramp mode in which the rate of infusion gradually increases, then remains constant, and then gradually decreases.

Additionally, many types of medications can be administered to a patient via the respiratory tract. Delivery of drugs to the lungs by way of inhalation is an important means of treating a variety of conditions, including such common local conditions as cystic fibrosis, pneumonia, bronchial asthma and chronic obstructive pulmonary disease and some systemic conditions, including hormone replacement, pain management, immune deficiency, erythropoiesis, diabetes, etc. Steroids, beta agonists, anti-cholinergic agents, proteins and polypeptides are among the drugs that are administered to the lungs for such purposes. Such drugs are commonly administered to the lung in the form of an aerosol of particles of respirable size (less than about 10 µm in diameter). The aerosol formulation can be presented as a liquid or a dry powder. In order to assure proper particle size in a liquid aerosol, particles can be prepared in respirable size and then incorporated into a colloidal dispersion either containing a propellant as a metered dose inhaler (MDI) or air, such as in the case of a dry powder inhaler (DPI). For MDI application, an aerosol formulation is placed into an aerosol canister equipped with a metered dose valve. In the hands of the patient the formulation is dispensed via an actuator adapted to direct the dose from the valve to the patient.

Delivery of medication via the respiratory tract may be preferred in many circumstances because medication delivered this way enters the bloodstream very rapidly. Delivery of medication to the lungs may also be preferred when the medication is used in a treatment of a disease or condition affecting the lungs in order to apply or target the medication as close as physically possible to the diseased area.

Aerosol delivery of a medication to a patient's respiratory tract also may be performed while the patient is intubated, i.e. when an endotracheal tube is positioned in the patient's trachea to assist in breathing. When an endotracheal tube is positioned in a patient, a proximal end of the endotracheal tube may be connected to a mechanical ventilator and the distal end is located in the trachea. An aerosol may be added to the airflow in the ventilator circuit of the endotracheal tube and carried by the patient's inhalation to the lungs. A significant amount of the aerosolized medication may be deposited inside the endotracheal tube and the delivery rate of the medicine to the lungs also remains relatively low and unpredictable.

Another use of an insufflator is to inflate a body cavity, like the abdominal cavity. Insufflation of the cavity is necessary to provide a working space for a surgeon to examine the contents of the cavity or operate within the cavity. Insufflating the abdominal cavity with gas, normally carbon dioxide, elevates the abdominal wall and pushes the contents of the region, such as the bowel and the liver, away from the areas of the cavity requiring the surgeon's attention. Various gas insufflators for use in the operating room are known. These insufflators infuse between 4 and 6 liters of carbon dioxide into the abdomen, creating a distention pressure of 15 mmHg (0.33 psi).

The carbon dioxide for an operating room insufflation unit is supplied by large pressurized tanks. Flow rate and pressure may be regulated by controls located on the insufflator units, and monitors located on the units display gas flow rate, gas pressure, and the total infusion volume. For use in a doctor's office or emergency room, it is desirable to have a compact hand-held insufflation unit. Such a simplified unit would provide an adequate volume of insufflation gas without the risk of over insufflation.

In addition to delivering medication via gravity-fed intravenous infusion, infusion pumps, inhalation, and insufflation, a drug may be delivered subcutaneously by way of an aerosolized or atomized medicament. Generally, a physician may insert a delivery tube within an incision or body cavity of a patient to administer the drug to the surface area of the body cavity.

As described above, there are a variety of means to administer medicaments to a patient. That is, therapeutic agents can be delivered intravenously, subcutaneously, or respiratorily. However, the distribution system of the present invention provides an apparatus and method of delivering pharmaceutical agents percutaneously to a desired location while providing thorough dispersion of the medicament over a large surface area.

Figure 24:
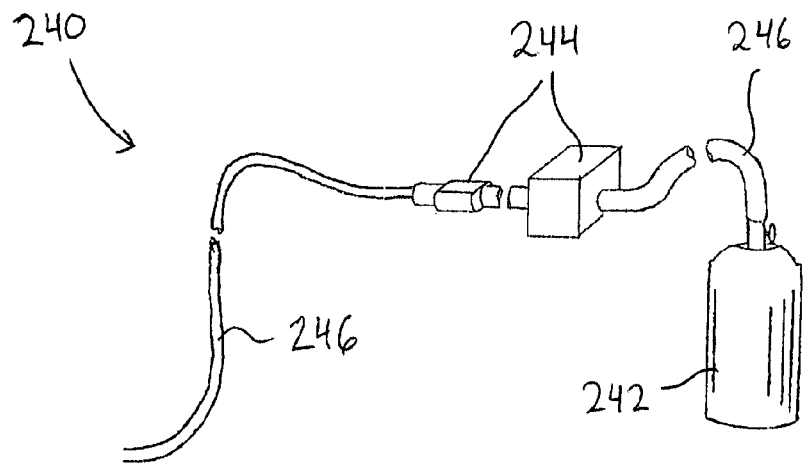
FIG. 24 illustrates an aerosol drug delivery system of the present invention.

FIG. 24 illustrates an exemplary embodiment of a drug distribution system 240 of the present invention. The system 240 includes an aerosol canister 242 with a medicament, a control unit 244, and interconnecting tubing 246. The canister 242 may be pressurized with a gas/medicament combination. The gas may be carbon dioxide, nitrogen, oxygen, or other biocompatible gas. The medicament or agent may be a gas, liquid, power, solid, particulate, granule, crystal, or gel. An example of a therapeutic/pharmaceutical agent includes a hemostatic agent, antibiotic, bone morphogenic protein, chemotherapeutic agent, anesthetic agent, agent that changes neovascularity, proteins, immunoglobulin, steroids, anti-inflammatory agent, angiogenesis factors, lidocaine, eqinephrine, ethrane, halofane, nitrous oxide, carbon dioxide, nitrogen, oxygen, opiates like OxyContin, morphine, Demerol, any agent described herein, and combinations thereof.

The control unit 244 may include a microprocessor and/or switches for controlling the release of the medicament. The microprocessor may automatically deliver the agent(s) within the body, while the switches allow an operator to administer agent(s) manually. The control unit 244 may control how the medicament is administered. That is, the medicament may be delivered in pulses, bursts, high pressure, low pressure, spray, stream, aerosolized, atomized, or combinations thereof. How the medicament is delivered determines the amount of tissue surface area that is covered by the agent. For example, stream burst delivery would cover a small target site, while a spray burst aerosolized delivery would cover a greater tissue area. The control unit may be remote controlled via a wire or RF, IR, optical, or microwave energy. The control unit may be operated by a physician, technician, and/or patient. The control unit may be time controlled for continuous or period drug delivery.

The interconnecting tubing 246 of the drug delivery system may be made of polymeric, metallic, composite, or ceramic material. The tubing 246 may be biodegradable, biostable, and/or expandable. Multi-lumen tubing may be used for delivery of two or more agents. The distal tip of the delivery tube may include a needle (steerable or curved), omni-directional ports, and an atomizing/dispersing tip.

Figure 25:
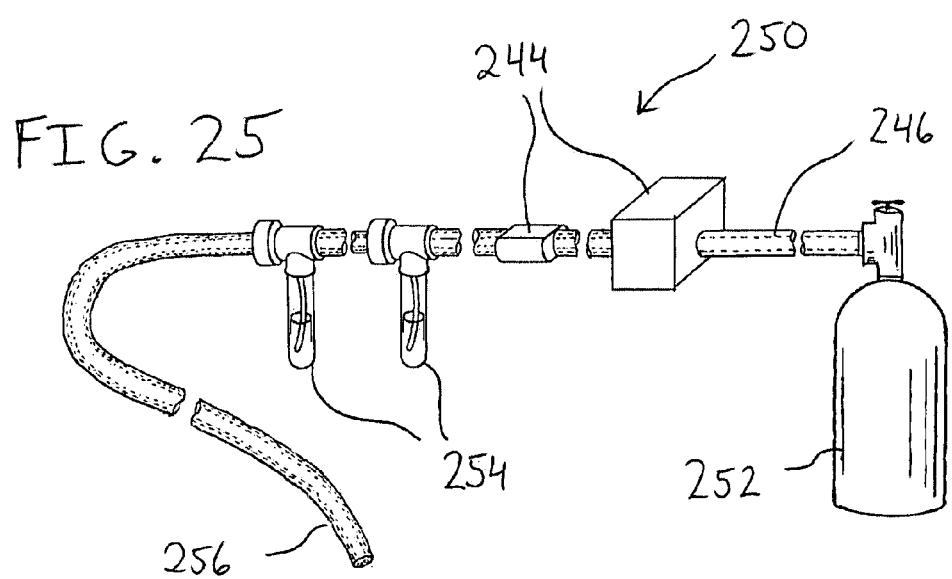
FIG. 25 shows a compressed gas drug delivery system.

Referring now to FIG. 25, a multi-medicament delivery system 250 is shown. The system includes a gas container 252, a control unit 244, two or more drug reservoirs 254, and connecting tubing 246. The container 252 includes a gas with or without a medicament. The gas may be any of the gaseous substances disclosed herein. The control unit 244 may include all or some of the characteristics of the control unit of FIG. 25. The drug reservoirs 254 may be refillable and include any of the therapeutic or pharmaceutical agents described herein. The tubing includes a plurality of lumens 256 for delivery of the plurality of agents.

Tissue Distraction

Figure 26:
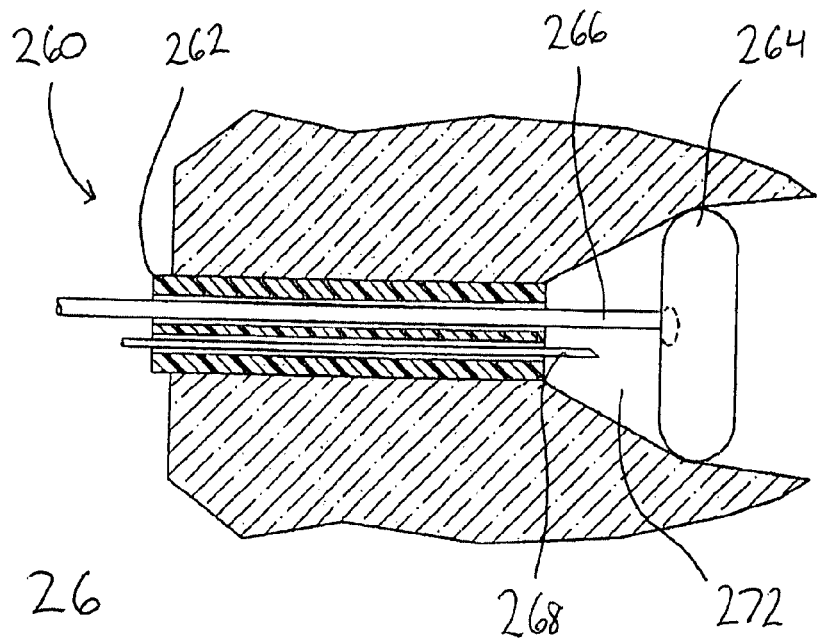
FIG. 26 is a cross sectional view of a distraction drug delivery system.
Figure 27:
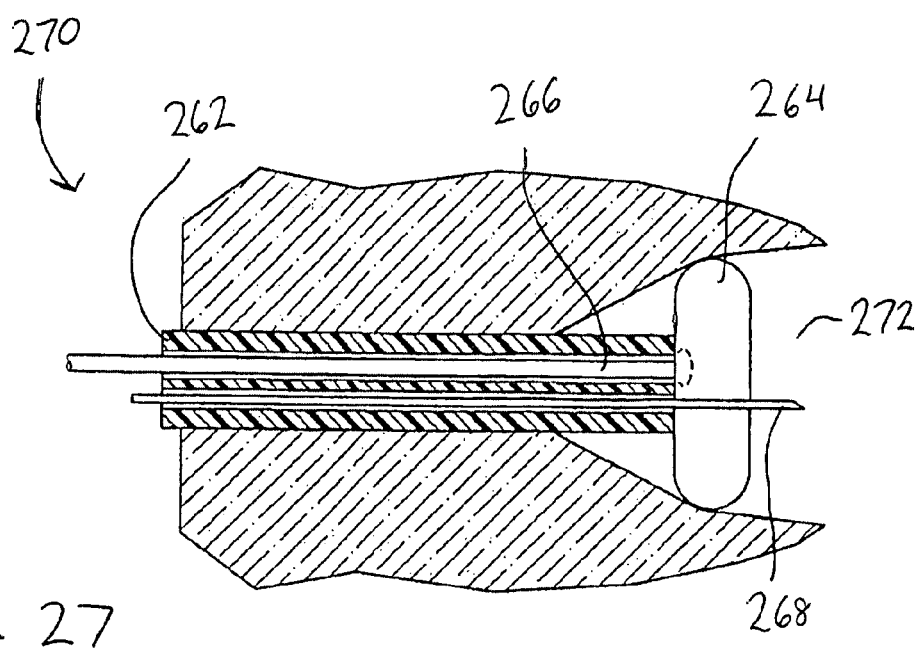
FIG. 27 is a cross sectional view of another distracting drug delivering system of the present invention.

FIGS. 26 and 27 illustrate tissue distraction systems for use with the drug delivery systems of the present invention. The distraction system 260 of FIG. 26 includes a multi-channel catheter/cannula 262, an expandable balloon 264, a balloon inflation tube 266, and a drug delivery tube 268. In use, the system 260 is inserted in tissue adjacent a body region 272 which require the administration of one or more medicaments. During insertion, the balloon 264 is deflated to minimize tissue displacement. Once positioned, the balloon 264 is inflated to distract tissue. The distal end of the drug delivery tube 268 is positioned proximal from the balloon 264 such that medicament may be administered to tissue located proximal to the balloon 264.

The distraction drug delivery system 270 of FIG. 27 is similar to the system of the FIG. 26 and includes similar structural features. In use, the system 270 is inserted in tissue adjacent a body region 272 which requires the administration of one or more medicaments. During insertion, the balloon 264 is deflated to minimize tissue displacement. Once positioned, the balloon 264 is inflated to distract tissue. The distal end of the drug delivery tube 268 is positioned distal from the balloon 264 such that medicament may be administered to tissue located distal to the balloon 264. The systems 260/270 of FIGS. 26 and 27 allow therapeutic and pharmaceutical agents to be delivered to a greater tissue surface area since the tissue is spaced apart by the inflated balloon.

Dispersion

Figure 28A:
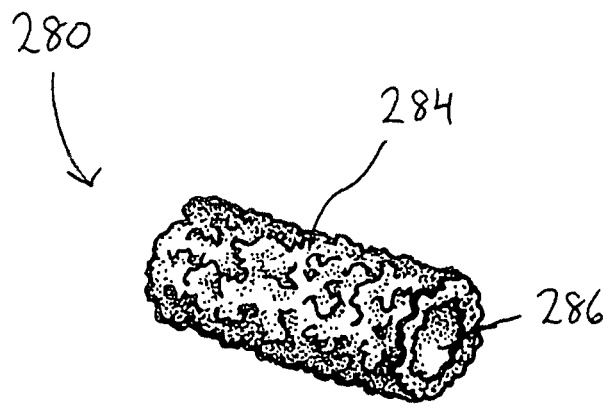
FIGS. 28A and 28B illustrate a omni-directional drug dispersal system.
Figure 28B:
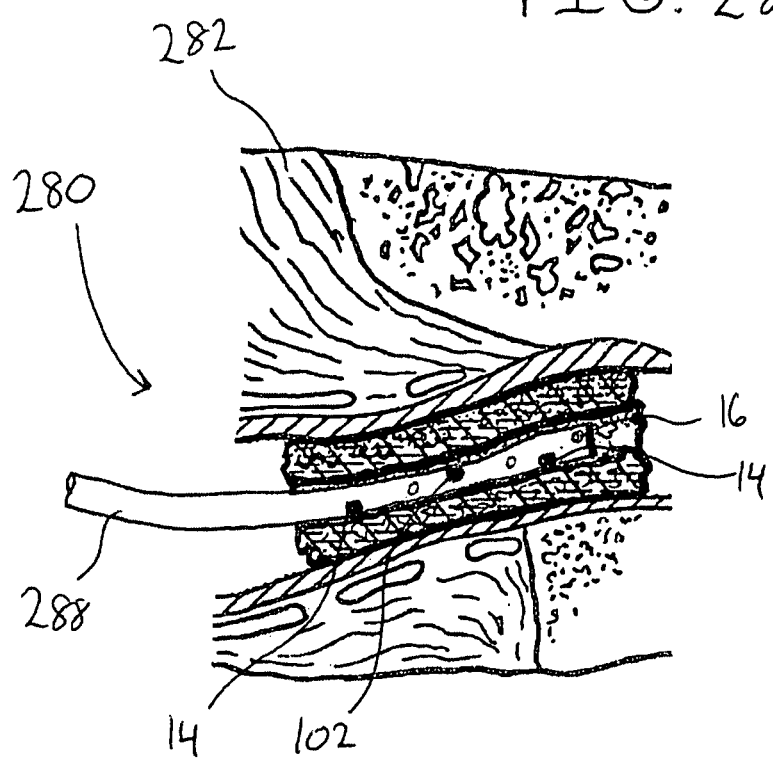

FIGS. 28A and 28B illustrate a drug dispersion member 280 for administering one or more medicaments to the surface of tissue. The dispersion member 280 includes porous material 284 for allowing medicaments to flow therethrough. The member 280 may be made of foam, fabric, polymer, metal, ceramic, composite, or combinations thereof. It may be biodegradable or biostable. The dispersion member 280 may include a channel 286 dimensioned for receiving a delivery tube 288 of a drug delivery system previously described. In FIG. 28B, the member 280 is implanted in tissue 282 such that the outer surface of the member contacts the tissue surface. The delivery tube 288 is inserted in the channel 286 of the member 280. The tube 288 may include microenvironment-controlling devices, such as sensors 14, magnets 102, heating/cooling units 18, drug ports 16, and pressure ports 16. With the tube positioned, one or more medicaments may be expelled from the tube 288 and captured by the porous material 284 of the disbursement member 280. The member and its pores function as a wick to carry the agent(s) to the adjacent tissue. The microenvironment of the adjacent tissue may be measured, changed, and monitored by the dispersion member.

Internal Aerosol Delivery

Figure 29A:
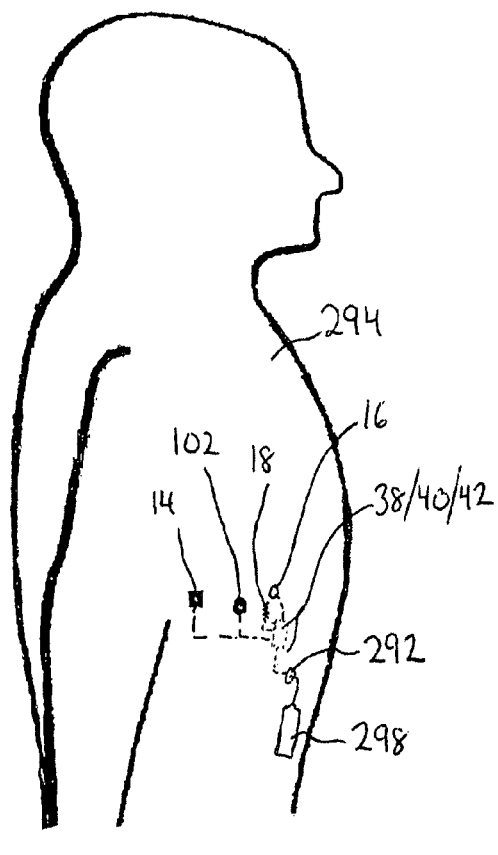
FIG. 29A shows a partially implanted drug delivery apparatus of the present invention.
Figure 29B:
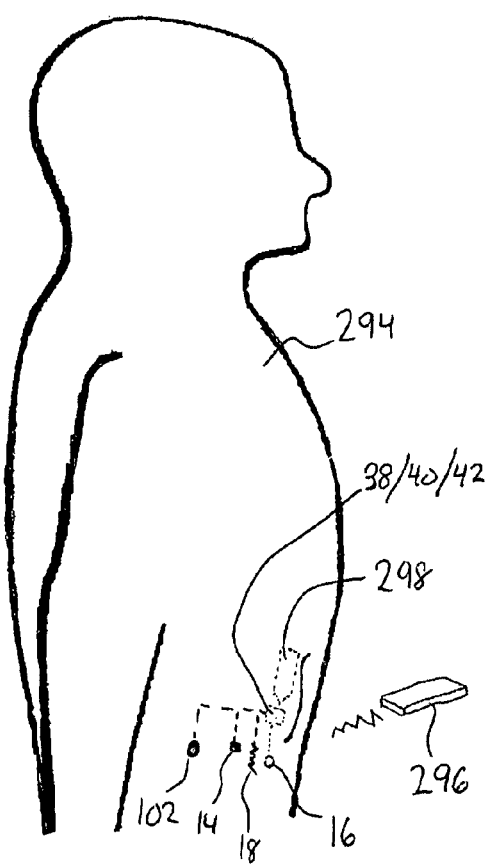
FIG. 29B illustrates a fully implanted, externally controlled drug delivery device.

The embodiments shown in FIGS. 24 and 25 were configured for external drug administration. However, in FIGS. 29A and 29B, implantable delivery systems are illustrated. The implantable systems include similar structural elements as the systems of FIGS. 24 and 25. In FIG. 29A, the control unit/reservoir 38/42, microenvironment-controlling devices, and tubing are implanted in the patient 294. A refill port 292 is positioned in the skin and is connected to the internal tubing. The medicament/gas canister 298 is connected to the refill port 292 for recharging the internal reservoir 40. The embodiment of FIG. 29B is completely implanted. The canister 298 along with the other components is positioned in the patient. The control unit 38 of the system may be operated with a remote 296 via RF, IR, optical, or microwave energy. The microenvironment of internal body tissue may be measured, changed, and monitored by the implantable delivery systems.

Generator Joint

Figures 30A, 30B:
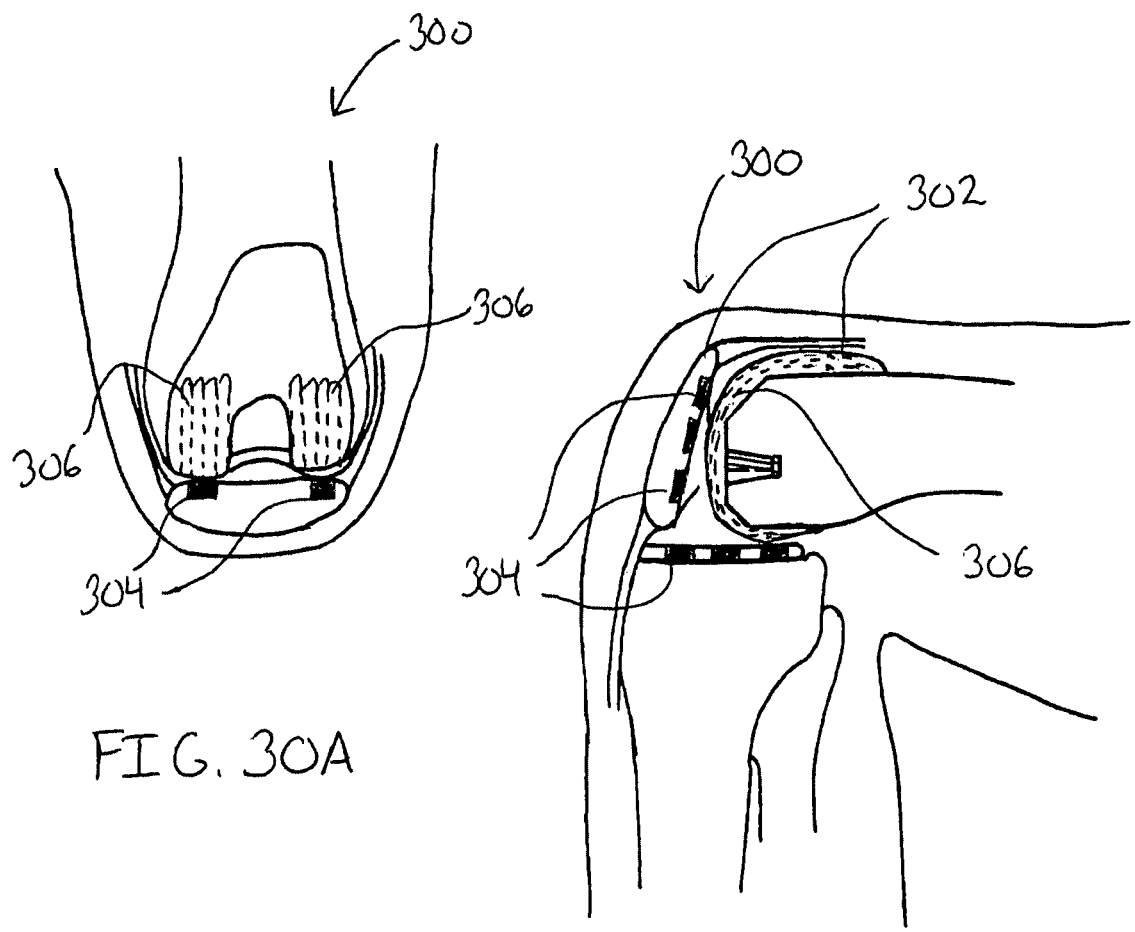
FIG. 30A is a top view of a generator joint.
FIG. 30B is a side view of the generator joint of FIG. 30A.

In a related invention, a generator joint 300 is illustrated in FIGS. 30A and 30B. A replacement component or total joint replacement implant 302 may include magnets 304 and winding 306 for generating electrical current. The joint may be the knee, shoulder, hip, spine, elbow, wrist, ankle, or a joint of the foot or hand. The electrical current may be used to power any of the microenvironment-controlling systems described herein or to power any other implant. In an exemplary embodiment, a total knee replacement implant 302 is shown. The implant components include magnets 304, windings 306, and electrical wires. As the knee is moved or rotated naturally, the relative movement of the magnets and windings create an electrical current. This current may be utilized to power sensors, heating/cooling units, electromagnets, drug pumps, or any other microenvironment-controlling device.

Fuel Cell

In a further related invention, a fuel cell may be used to power the microenvironment-controlling apparatus of the present invention. Fuel cells generate electricity by combining hydrogen with oxygen. In an exemplary embodiment, the fuel cell runs on alcohol such as methanol. The power source for the devices of the present invention may also be a hybrid of battery power and a fuel cell.

Heat Probe

Figure 31:
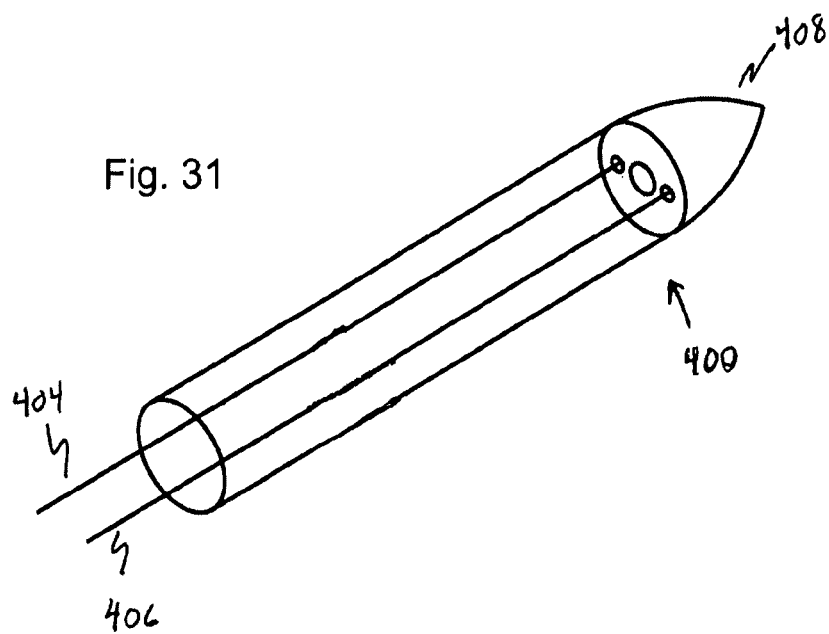
FIG. 31 illustrates a device in accordance with the invention for controlling a microclimate.
Figure 32:
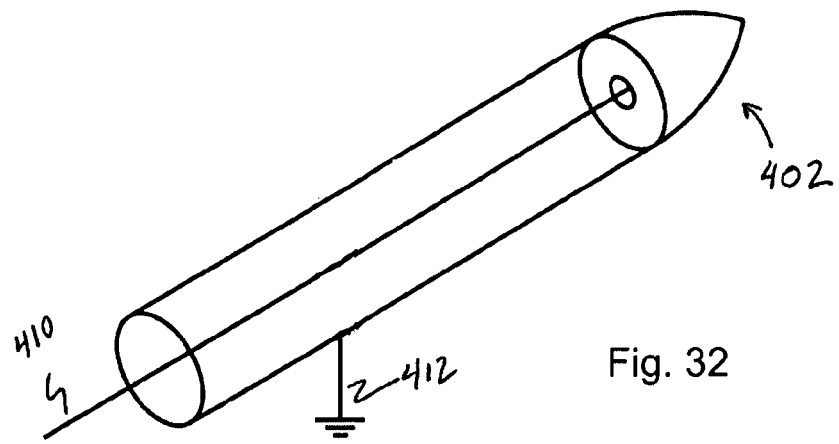
FIG. 32 is an alternative to the device of FIG. 31, having a grounded case.

FIGS. 31 and 32 depict a needle shaped device 400,402 for microclimate heating in the body. Wires 404,406 convey electrical energy to a heater at the needle tip. In needle 402, a single wire 410 provides power in combination with a chassis ground 412, enabling the needle to have a more narrow diameter. Needles 400,402 may be combined with systems described herein, where it is advantageous to control temperature. Wires 404,406, and 410 are controllable by a system microcontroller, as described above.

Magnetic Heating

Figure 33:
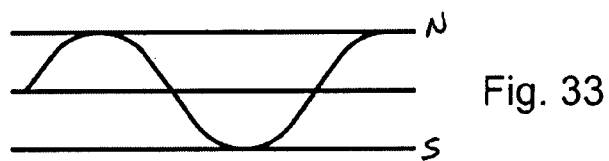
FIG. 33 illustrates a waveform illustrating a change in magnetic waveform operative to generate heat.
Figure 34:
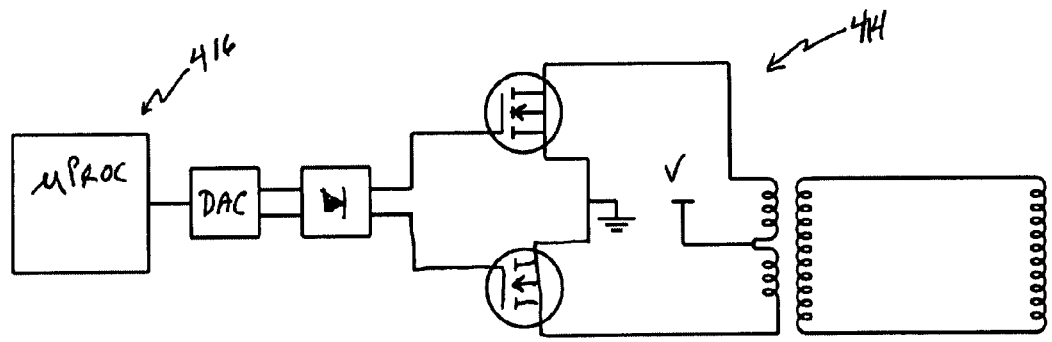
FIG. 34 illustrates a circuit to create and control a sinusoidal signal.
Figure 35:
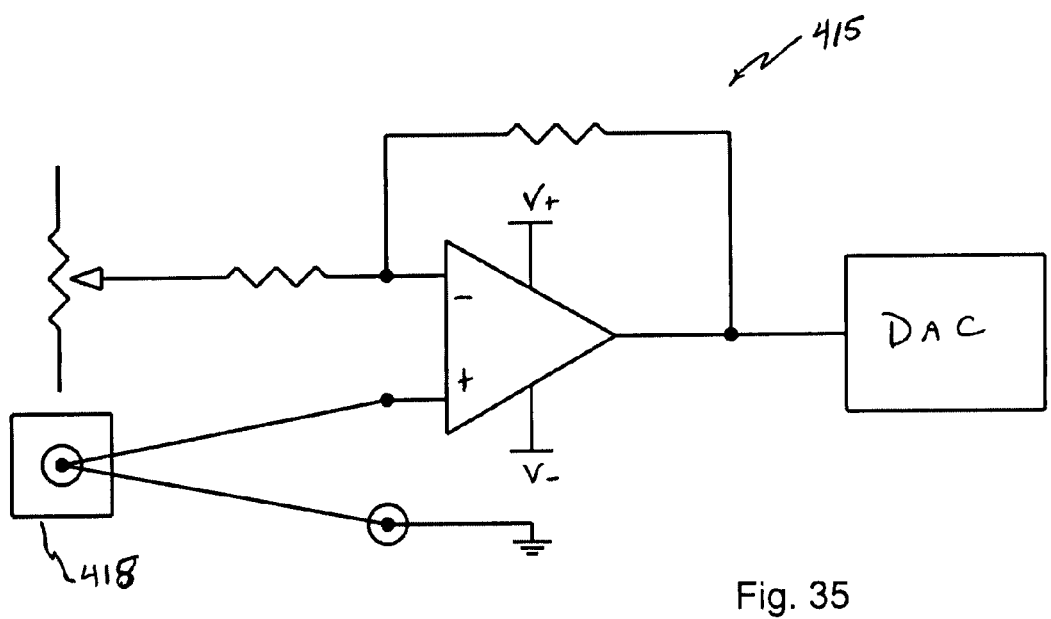
FIG. 35 illustrates a circuit for monitoring temperature.

FIGS. 33 and 34 illustrate a method of heating magnetic material implanted proximate the site for which microclimate control is desired. FIG. 3 illustrates a sinusoidal waveform representative of the change in magnetic pull. By rapidly changing the poles, indicate as N north and S south, magnetic particles within the body are excited and thus generate heat. Circuit 414 is illustrative of a means for such rapid polar changing, under microprocessor 416 control. As can be seen in FIG. 35, a circuit 415 may be used to precisely monitor the temperature generated, incorporating thermocouple 418.

Figure 36:
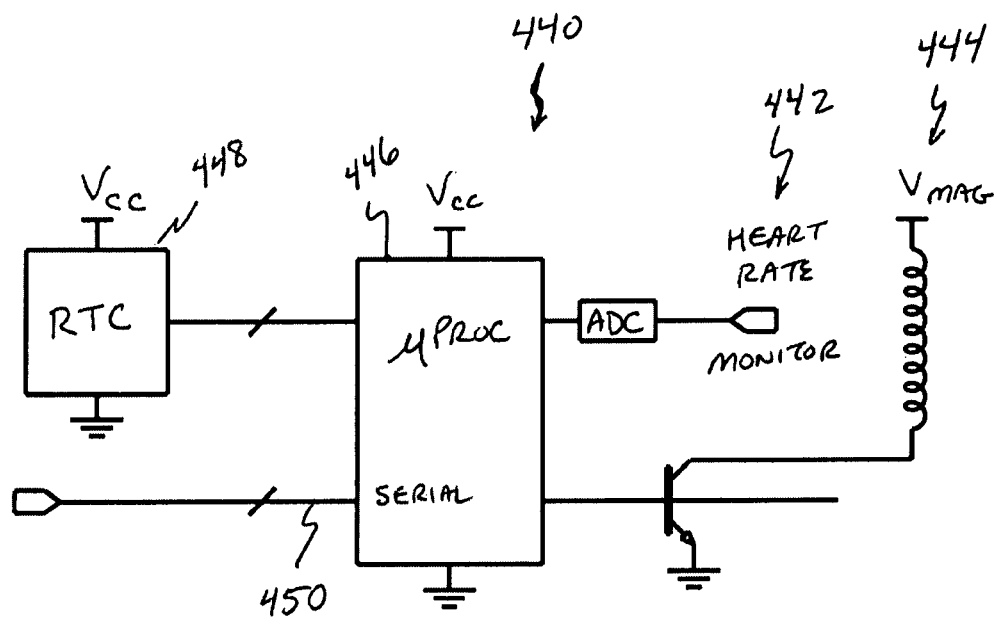
FIG. 36 illustrates a control circuit for magnet control, with heart rate input, and controls.
Figure 37:
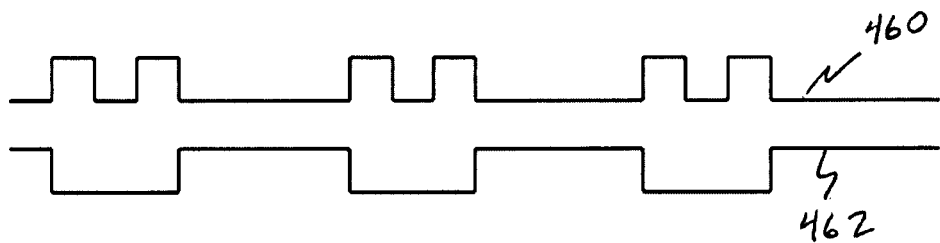
FIG. 37 illustrates heart monitor and control signals.

It may be advantageous to coordinate or correlate magnetic pulses with the heart rate, for improved efficacy of a therapeutic substance delivered as described above. With reference to FIG. 36, a circuit 440 is shown, with a heart rate monitor 442, magnetic field output 444, microprocessor 446, real time clock 448 for microprocessor control and power saving, and a serial interface 450 for downloading a delivery profile. FIG. 37 illustrates a corresponding signal profile, with trace 460 indicating the heart beat, and trace 462 indicating the programmed delivery profile correlated therewith.

Energy Delivery

Figure 38:
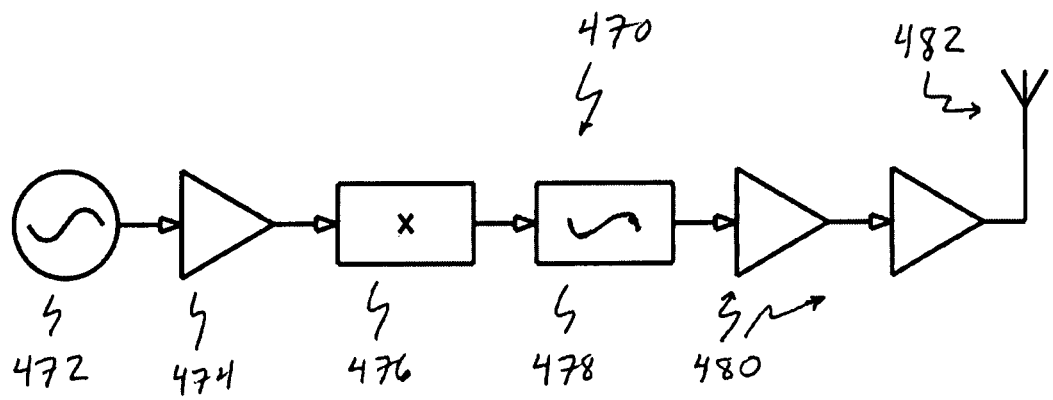
FIG. 38 illustrates a radio frequency energy delivery circuit.

With reference to FIG. 38, a circuit 470 is illustrated, operative to transmit radio frequency (RF) energy. Illustrated are frequency generator 472, pre-amplifier 474, frequency multiplier 476, power amplifiers 480, and output antenna 482. In this application, an implant (not shown) has an antenna that would receive the energy transmitted at 482 to power the implant, and or to directly warm the tissue proximate the implant.

Figure 39:
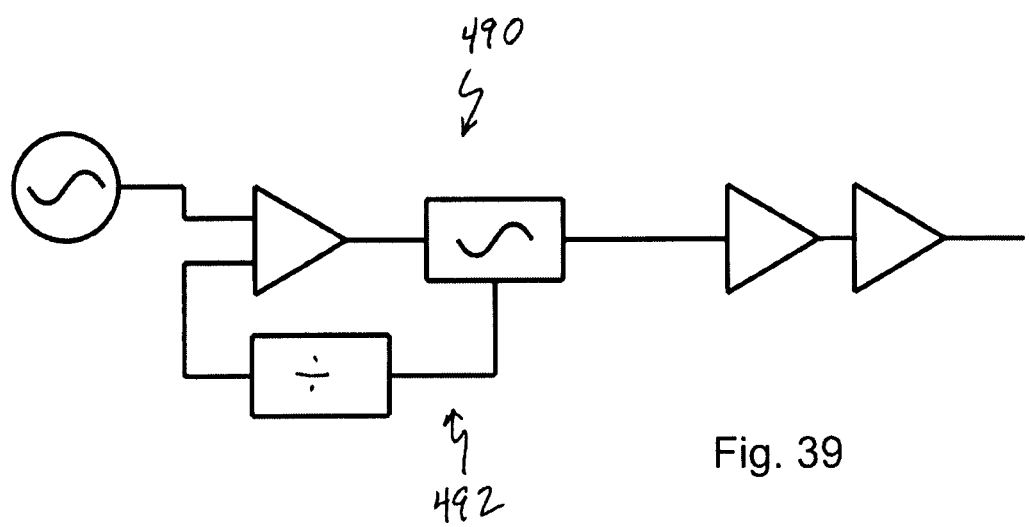
FIG. 39 illustrates an ultrasonic generator circuit.

FIG. 39 illustrates and ultrasonic generator circuit having components analogous to FIG. 38, with the inclusion of a feedback loop 492 operative to create a phase lock loop signal. Feedback mechanisms may be based on constant phase, mm impedance or other methods.

Figure 40:
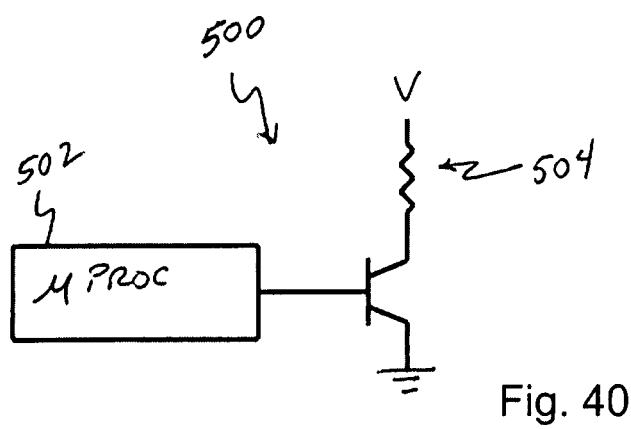
FIG. 40 illustrates a resistive heater circuit.

FIG. 40 illustrates a resistive heater circuit 500 including a microprocessor/microcontroller 502 and heating element 504.

It is contemplated the microenvironment-controlling systems of the present invention may be used with and integrated with the methods and devices disclosed in U.S. Provisional Application No. 60/765,857 entitled "Surgical Fixation Device" filed on Feb. 7, 2006. In the '857 document, various thermoplastic fixation devices are disclosed. The fixation devices may be, but are not limited to, degradable, biodegradable, bioerodible, bioabsorbable, mechanically expandable, hydrophilic, bendable, deformable, malleable, riveting, threaded, toggling, barded, bubbled, laminated, coated, blocking, pneumatic, one-piece, multi-component, solid, hollow, polygon-shaped, pointed, self-introducing, and combinations thereof. Also, the devices may include, but are not limited to, metallic material, polymeric material, ceramic material, composite material, body tissue, synthetic tissue, hydrophilic material, expandable material, compressible material, heat bondable material, and combinations thereof.

The methods and devices disclosed in the '857 document may be used in conjunction with any surgical procedure of the body. The fastening and repair of tissue or an implant may be performed in connection with surgery of a joint, bone, muscle, ligament, tendon, cartilage, capsule, organ, skin, nerve, vessel, or other body parts. For example, tissue may be repaired during intervertebral disc surgery, knee surgery, hip surgery, organ transplant surgery, bariatric surgery, spinal surgery, anterior cruciate ligament (ACL) surgery, tendon-ligament surgery, rotator cuff surgery, capsule repair surgery, fractured bone surgery, pelvic fracture surgery, avulsion fragment surgery, shoulder surgery, hernia repair surgery, and surgery of an intrasubstance ligament tear, annulus fibrosis, fascia lata, flexor tendons, etc.

It is contemplated that the devices and methods of the present invention be applied using minimally invasive incisions and techniques to fasten muscles, tendons, ligaments, bones, nerves, and blood vessels. A small incision(s) may be made adjacent the damaged tissue area to be repaired, and a tube, delivery catheter, sheath, cannula, or expandable cannula may be used to perform the methods of the present invention. U.S. Pat. No. 5,320,611 entitled "Expandable Cannula Having Longitudinal Wire and Method of Use" discloses cannulas for surgical and medical use expandable along their entire lengths. The cannulas are inserted through tissue when in an unexpanded condition and with a small diameter. The cannulas are then expanded radially outwardly to give a full-size instrument passage. Expansion of the cannulas occurs against the viscoelastic resistance of the surrounding tissue. The expandable cannulas do not require a full depth incision, or at most require only a needle-size entrance opening.

U.S. Pat. Nos. 5,674,240; 5,961,499; and 6,338,730 also disclose cannulas for surgical and medical use expandable along their lengths. The cannula can be provided with a pointed end portion and can include wires having cores which are enclosed by jackets. The jackets are integrally formed as one piece with a sheath of the cannula. The cannula may be expanded by inserting members or by fluid pressure. An expandable chamber may be provided at the distal end of the cannula. The above mentioned patents are hereby incorporated by reference.

In addition to using a cannula with the present invention, an introducer may be utilized to position implants at a specific location within the body. U.S. Pat. No. 5,948,002 entitled "Apparatus and Method for Use in Positioning a Suture Anchor" discloses devices for controlling the placement depth of a fastener. Also, U.S. patent application Ser. No. 10/102,413 discloses methods of securing body tissue with a robotic mechanism. The above-mentioned patent and application are hereby incorporated by reference. Another introducer or cannula which may be used with the present invention is the VersaStep® System by Tyco® Healthcare.

The present invention may also be utilized with minimally invasive surgery techniques disclosed in U.S. Pat. Nos. 6,702,821; 6,770,078; and 7,104,996. These patent documents disclose, inter alia, apparatus and methods for minimally invasive joint replacement. The femoral, tibial, and/or patellar components of a knee replacement may be fastened or locked to each other and to adjacent tissue using fixation devices disclosed herein and incorporated by reference. Furthermore, the methods and devices of the present invention may be utilized for repairing, reconstructing, augmenting, and securing tissue or implants during and "on the way out" of a knee replacement procedure. For example, the anterior cruciate ligament and other ligaments may be repaired or reconstructed; quadriceps mechanisms and other muscles may be repaired; a damaged rotator cuff may be mended. The patent documents mentioned above are hereby incorporated by reference.

It is further contemplated that the present invention may be used in conjunction with the devices and methods disclosed in U.S. Pat. No. 5,329,846 entitled "Tissue Press and System" and U.S. Pat. No. 5,269,785 entitled "Apparatus and Method for Tissue Removal." For example, an implant of the present invention may include tissue harvested, configured, and implanted as described in the patents. The above-mentioned patents are hereby incorporated by reference.

Additionally, it is contemplated that the devices and methods of the present invention may be used with heat bondable materials as disclosed in U.S. Pat. No. 5,593,425 entitled "Surgical Devices Assembled Using Heat Bondable Materials." For example, the implants of the present invention may include thermoplastic material. The material may be deformed to secure tissue or hold a suture or cable. The fasteners made of heat bondable material may be mechanically crimped, plastically crimped, or may be welded to a suture or cable with RF (Bovie devices), laser, ultrasound, electromagnet, ultraviolet, infrared, electro-shockwave, or other known energy. The welding may be performed in an aqueous, dry, or moist environment. The welding device may be disposable, sterilizable, single-use, and/or battery-operated. The above-mentioned patent is hereby incorporated by reference.

Furthermore, the methods of the present invention may be performed under indirect visualization, such as endoscopic guidance, computer assisted navigation, magnetic resonance imaging, CT scan, ultrasound, fluoroscopy, X-ray, or other suitable visualization technique. The implants of the present invention may include a radiopaque material for enhancing indirect visualization. The use of these visualization means along with minimally invasive surgery techniques permits physicians to accurately and rapidly repair, reconstruct, augment, and secure tissue or an implant within the body. U.S. Pat. Nos. 5,329,924; 5,349,956; and 5,542,423 disclose apparatus and methods for use in medical imaging. Also, the present invention may be performed using robotics, such as haptic arms or similar apparatus. The above-mentioned patents are hereby incorporated by reference.

All references cited herein are expressly incorporated by reference in their entirety.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention.

What is claimed is:

1. A system for administering therapy to a human body by controlling an environmental parameter of a localized area inside the body, comprising: at least one sensor for sensing environmental parameters proximate the localized area; at least one effector for changing the at least one environmental parameter, implantable proximate the localized area, said at least one environmental parameter including pH; at least one controller, operatively associated with said at least one sensor, operative to control said at least one effector; whereby when said at least one effector changes said at least one environmental parameter, the efficacy of the therapy is improved, and wherein the elements of the system are connected to an object placed inside the body, selected from the group consisting of: endoscope, intramedullary rod, fastener, plate, joint replacement, spinal implant, acetabular replacement, or sheet wrapped around a tubular body structure.

2. The system of claim 1, wherein a second environmental parameter is changed, and said second environmental parameter is selected from the group consisting of: temperature, moisture, humidity, oxygen level, oxygenase, carbon dioxide level, rate of blood flow, nutrient level, osmolarity, pressure, vascular permeability, electrical charge, and therapeutic agent level.

3. The system of claim 2, wherein said second environmental parameter is selected to be temperature, and said at least one effector for changing the temperature is operative, by changing the temperature proximate the localized area, to change the pH proximate the localized area, in a controlled manner using said sensor and controller, wherein the efficacy of the therapeutic substance released proximate the localized area is improved.

4. The system of claim 1, where said at least one effector for changing environmental parameter is selected from the group consisting of: resistive heater, ultrasonic heater, IR heater, RF heater, microwave heater, convection cooling device, conduction cooling device, electronic cooling device, Peltier cooling device, suction device, charged particles, metallic ions, and charged ions.

5. The system of claim 1, further including release means operative to release a therapeutic substance proximate the localized area of the body, wherein said therapeutic substance is selected from the group consisting of: cellular nutrient, vasodilator, vasoconstrictor, antibiotics, hydroxypatite, anti-inflammatory agents, steroids, antibiotics, analgesic agents, chemotherapeutic agents, bone morphogenetic protein, demineralized bone matrix, collagen, growth factors, autogenetic bone marrow, progenitor cells, calcium sulfate, immu-suppressants, fibrin, osteoinductive materials, apatite compositions, fetal cells, embryonic cells, stem cells, enzymes, proteins, hormones, germicides, non-proliferative agents, anti-coagulants, anti-platelet agents, tyrosine kinase inhibitors, anti-infective agents, anti-tumor agents, anti-leukemic agents.

6. The system of claim 5, further comprising:
at least one port proximate the localized area, connected to said release means, operative to conduct released therapeutic substance proximate the localized area of a body.

7. The system of claim 5, wherein when the temperature proximate the localized area of the body is changed, the efficacy of said therapeutic substance is changed.

8. The system of claim 5, wherein said at least one controller is further operative to control the rate, frequency and duration of release of said means operative to release a therapeutic substance;
whereby when the temperature proximate the localized area is changed, the rate at which said therapeutic substance is released is changed.

9. The system of claim 1, further comprising:
an endoscope having a plurality of lumens;
a guide wire extending through one of said lumens, operative to support at least one of said at least one end effector;
whereby said guide wire may be manipulated to position at least one of said at least one end effector in a desired position beyond the end of said endoscope inside the body.

10. The system of claim 1, further comprising:
an endoscope having a plurality of lumens;
a guide wire extending through one of said lumens, operative to support at least one of said at least one sensor;
whereby said guide wire may be manipulated to position at least one of said at least one sensor in a desired position beyond the end of said endoscope inside the body.

11. The system of claim 1, wherein said controller is controlled by a method selected from the group consisting of: manual controls, wired remote, radio frequency telemetry, acoustic telemetry, microwave telemetry, internal programming.

12. The system of claim 1, wherein the effector is an electrical transmitter.

13. The system of claim 1, wherein the effector is battery operated.

14. The system of claim 1, wherein the effector is positioned internal or external to the body.

15. The system of claim 1, wherein the localized area of the body is the stomach.

16. The system of claim 15, wherein the therapeutic benefit is a reduction in the patient's appetite.

17. A system for administering therapy to a human body by controlling an environmental parameter of a localized area inside the body, comprising: at least one sensor for sensing environmental parameters proximate the localized area; at least one effector for changing the at least one environmental parameter, implantable proximate the localized area, said at least one environmental parameter including pH; at least one controller, operatively associated with said at least one sensor, operative to control said at least one effector; whereby when said at least one effector changes said at least one environmental parameter, the efficacy of the therapy is improved, and further including a sheet wrapped around a blood vessel, wherein the wrapped sheet constricts a tubular structure decreasing a diameter of same, thereby increasing a rate of blood flow through a constricted space.

18. A system for administering therapy to a human body by controlling an environmental parameter of a localized area inside the body, comprising: at least one sensor for sensing environmental parameters proximate the localized area; at least one effector for changing the at least one environmental parameter, implantable proximate the localized area, said at least one environmental parameter including pH; at least one controller, operatively associated with said at least one sensor, operative to control said at least one effector; whereby when said at least one effector changes said at least one environmental parameter, the efficacy of the therapy is improved, wherein said at least one effector includes a suction device operative to create a negative pressure proximate the localized area of the body, whereby the efficacy of the therapy is improved, wherein said suction device is operative to create vasodilation proximate a location where said suction is proximate body tissue, and thereby creates vasoconstriction distal to the location of vasodilation, and wherein said suction device further includes: means for cooperating with a knee joint including a chamber connected with a first side of the knee joint; a valve connected with said chamber; a connector connected to said chamber and a second side of the knee joint; a tube connected to said chamber, having a distal end extending to the localized area of the body; whereby movement of the joint produces suction at the distal end of said tube.

* * * * *